US010308969B2

(12) United States Patent
Ejima et al.

(10) Patent No.: US 10,308,969 B2
(45) Date of Patent: Jun. 4, 2019

(54) METHOD FOR PREPARING POLYMERIC PROTEIN COMPOSED OF MONOMERIC PROTEIN PRODUCED BY FUSING PROTEIN HAVING IMMUNOGLOBULIN FOLD STRUCTURE TO PROTEIN CAPABLE OF SERVING AS SUBUNIT STRUCTURE

(71) Applicant: AJINOMOTO CO., INC., Tokyo (JP)

(72) Inventors: Daisuke Ejima, Kawasaki (JP); Haruna Sato, Kawasaki (JP); Kouhei Tsumoto, Tokyo (JP); Masayo Date, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 204 days.

(21) Appl. No.: 14/104,139

(22) Filed: Dec. 12, 2013

(65) Prior Publication Data

US 2014/0099672 A1    Apr. 10, 2014

Related U.S. Application Data

(63) Continuation of application No. PCT/JP2012/066121, filed on Jun. 25, 2012.

(30) Foreign Application Priority Data

Jun. 23, 2011  (JP) ................................. 2011-139837

(51) Int. Cl.
*C12P 21/00* (2006.01)
*C07K 14/36* (2006.01)
*C07K 16/40* (2006.01)
*C07K 1/113* (2006.01)
*C12P 21/02* (2006.01)

(52) U.S. Cl.
CPC ............ *C12P 21/00* (2013.01); *C07K 1/1136* (2013.01); *C07K 14/36* (2013.01); *C07K 16/40* (2013.01); *C12P 21/02* (2013.01); *C07K 2317/622* (2013.01); *C07K 2319/00* (2013.01)

(58) Field of Classification Search
None
See application file for complete search history.

(56) References Cited

U.S. PATENT DOCUMENTS

| 8,084,032 | B2 | 12/2011 | Yumioka et al. |
| 8,105,802 | B2 | 1/2012 | Umezawa et al. |
| 8,435,527 | B2 | 5/2013 | Yumioka et al. |
| 8,470,328 | B2 | 6/2013 | Yumioka et al. |
| 8,580,537 | B2 | 11/2013 | Suzuki et al. |
| 8,975,383 | B2 * | 3/2015 | Yumioka ............... C07K 1/1136 435/69.1 |
| 2003/0095977 | A1 * | 5/2003 | Goshorn ............ A61K 47/48353 424/185.1 |
| 2007/0184525 | A1 | 8/2007 | Date et al. |
| 2008/0318300 | A1 | 12/2008 | Koyama et al. |
| 2010/0143970 | A1 | 6/2010 | Yokoyama et al. |
| 2011/0077384 | A1 | 3/2011 | Yumioka et al. |
| 2013/0035381 | A1 | 2/2013 | Ejima et al. |
| 2014/0349371 | A1 | 11/2014 | Yumioka et al. |

FOREIGN PATENT DOCUMENTS

| CN | 102089319 A | 6/2011 |
| EP | 2281827 A1 | 2/2011 |
| WO | WO2009/136568 | 11/2009 |
| WO | WO2012/176919 | 12/2012 |

OTHER PUBLICATIONS

Office Action from Chinese Patent App. No. 201280030917.5 (dated Oct. 2014).
Notification of Reason for Rejection from Japanese Patent App. No. 2013-521655 (dated Jun. 24, 2015) with English translation thereof.
Kudou, M., et al., "Refolding single-chain antibody (scFv) using lauroyl-L-glutamate as a solubilization detergent ad arginine as a refolding additive," Protein Expression and Purification 2011;77:68-74.
Tsumoto, K., et al., "Solubilization of active green fluorescent protein from insoluble particles by guanidine and arginine," Biochem. Biophys. Res. Comm. 2003;312:1383-1386.
Supplementary European Search Report for European Patent App. No. 12803011.1 (dated Oct. 15, 2014).
Beck, A., et al., "Strategies and challenges for the next generation of therapeutic antibodies," Nature Rev. Immunol. 2010;10:345-352.
Bird, R. E., et al., "Single-Chain Antigen-Binding Proteins," Science 1988;242:423-426.
Huston, J. S., et al., "Protein engineering of antibody binding sites: Recovery of specific activity in an anti-digoxin single-chain Fv analogue produced in *Escherichia coli*," Proc. Natl. Acad. Sci. USA 1988;85:5879-5883.
Kipriyanov, S. M., et al., "Affinity enhancement of a recombinant antibody: formation of complexes with multiple valency by single-chain Fv fragment-core streptavidin fusion," Protein Engineering 1996;9(2):203-211.
Meyer, D. L., et al., "Reduced antibody response to streptavidin through site-directed mutagenesis," Protein Science 2001;10:491-503.

(Continued)

*Primary Examiner* — Yunsoo Kim
(74) *Attorney, Agent, or Firm* — Cermak Nakajima & McGowan LLP; Shelly Guest Cermak

(57) ABSTRACT

The present invention provides a method for producing a multimeric protein composed of a monomeric protein, wherein the monomeric protein is obtained by fusing a protein having an immunoglobulin fold structure to a protein that can serve as a subunit structure, the method including the steps of:
(A) preparing the monomeric protein having an insoluble granular form in cells of a microorganism;
(B) solubilizing the monomeric protein prepared in step (A) with an aqueous solution containing lauroyl-L-Glu;
(C) diluting a solution obtained in step (B) in a buffer containing arginine hydrochloride to lower a concentration of lauroyl-L-Glu; and
(D) replacing a solvent of a solution obtained in step (C) with a buffer using gel filtration chromatography or the like.

6 Claims, 8 Drawing Sheets

(56) References Cited

OTHER PUBLICATIONS

Pack, P., et al., "Miniantibodies: Use of Amphipathic Helices to Produce Functional, Flexibly Linked Dimeric Fv Fragments with High Avidity in *Escherichia coli*," Biochem. 1992;31(6):1579-1584.
Rheinnecker, M., et al., "Multivalent Antibody Fragments with High Functional Affinity for a Tumor-Associated Carbohydrate Antigen," J. Immunol. 1996;157:2989-2997.
Schultz, J., et al., "A Tetravalent Single-chain Antibody-Streptavidin Fusion Protein for Pretargeted Lymphoma Therapy," Cancer Res. 2000;60:6663-6669.
Skerra, A., et al., "Assembly of a Functional Immunoglobulin Fv Fragment in *Escherichia coli*," Science 1988;240:1038-1041.
Stayton, P. S., et al., "Molecular engineering of proteins and polymers for targeting and intracellular delivery of therapeutics," J. Controlled Release 2000;65:203-220.
Won, J. S., et al., "B3(Fab)-streptavidin Tetramer Has Higher Binding Avidity than B3(scFv)-streptavidin Tetramer," Bull. Korean Chem. Soc. 2009;30(5):1101-1106.
International Search Report and Written Opinion for PCT Patent App. No. PCT/JP2012/066121 (dated Sep. 25, 2012).

\* cited by examiner

METHOD FOR PREPARING POLYMERIC PROTEIN COMPOSED OF MONOMERIC PROTEIN PRODUCED BY FUSING PROTEIN HAVING IMMUNOGLOBULIN FOLD STRUCTURE TO PROTEIN CAPABLE OF SERVING AS SUBUNIT STRUCTURE

This application is a Continuation of, and claims priority under 35 U.S.C. § 120 to, International Application No. PCT/JP2012/066121, filed Jun. 25, 2012, and claims priority therethrough under 35 U.S.C. § 119 to Japanese Patent Application No. 2011-139837, filed Jun. 23, 2011, the entireties of which are incorporated by reference herein.

BACKGROUND OF THE INVENTION

Field of the Invention

The present invention relates to a method for producing a multimeric protein, which includes a monomeric protein obtained by fusing a first protein having an immunoglobulin fold structure to a second protein that can serve as a subunit structure.

Brief Description of the Related Art

Therapeutic antibodies have been successful because of their high therapeutic effect and low risk of side effects, but now have a problem of high medical fees due to the high production cost. There are other problems such as the therapeutic effect of such antibodies is limited to a relatively narrow range of diseases such as leukemia and autoimmune diseases, and the antibodies are not so effective against solid cancers and the like in which the distribution of a drug to the tissues is limited.

After the production of antibody fragments in *Escherichia coli* became possible in 1988 (Science, 240, 1038-1041 (1988), Proceedings of the National Academy of Sciences U.S.A., 85, 5879-5883 (1988), and Science, 242, 423-426 (1988)), modified antibodies (antibody fragments) having a high tissue distribution property and a lower molecular weight were developed. Many antibody fusion proteins have been proposed, which are obtained by fusing an antibody fragment to an anticancer agent, toxin, radioisotope, prodrug activating enzyme, or the like to obtain a higher cancericidal effect.

However, although the bivalent binding of naturally occurring antibodies serves as a basis of demonstrating a high affinity for a target antigen and excellent biokinetics, the binding activity to a target antigen of artificially produced monovalent antibody fusion proteins is far from the binding activity of naturally occurring antibodies.

Hence, recently, efforts have been actively made to produce multivalent low-molecular-weight modified antibodies and antibody fusion proteins (Nature Reviews Immunology, 10 345-352 (2010)). If it is possible to produce multivalent molecules like antibodies using a microorganism at a low cost, both a high performance and a low medical fee could be achieved.

Methods are known for producing multivalent molecules by utilizing the association of an antibody structure itself like those of antibodies mimicking diabody, triabody, or an immunoglobulin M. Other methods include a method for obtaining multivalent molecules by fusing a fragment structure of an antibody to an associative protein. Examples of such fusion include one utilizing dimerization via a leucine zipper structure linked to a single-chain antibody fragment of variable region (scFv), or via another design (Biochemisry (Mosc), 31, 1579-1584 (1992)), one achieved through a human p53-derived tetrameric α-helix structure (Journal of Immunogy, 157, 2989-2997 (1996))), one utilizing tetramerization of microorganism-derived streptavidin, and the like. Particularly, regarding the method in which streptavidin is fused, improved performances (such as increased stability and solubility, and decreased immunogenicity) have been already achieved by modifying the structure of streptavidin (Journal of Controlled Release 65, 203-220 (2000)). A protein fused to streptavidin enables drug pre-targeting using a biotin molecule, which binds to streptavidin with a high affinity. Thus, the fusion protein is one of the most promising multivalent fusion proteins (Journal of Controlled Release 65, 203-220 (2000)).

A problem thereof is that when a multivalent fusion protein is produced using a microorganism such as *Escherichia coli*, insoluble proteins are formed in cells of the microorganism in many cases. The insoluble proteins in cells of the microorganism have lost the activity and/or stability. Accordingly, if such proteins are used as a pharmaceutical preparation or the like, refolding operations for reconstructing the active structure are additionally required.

Schultz et al. have reported an example where an active form which is soluble in cells of *Escherichia coli* was produced by contriving a peptide linker in the scFv to be bound to streptavidin and the arrangement order of the H and L chains (Cancer Research, 60, 6663-6669 (2000)). Nevertheless, it is known that if altered to a modified form, streptavidin becomes insoluble in cells of *Escherichia coli* (Protein Science 10, 491-503 (2001)). Hence, it seems that refolding operations are required for streptavidin fusion proteins to be practically used.

In view of such circumstances, Choe et al. studied an example where a modified streptavidin fusion protein was refolded (Bulletin of Korean Chemical Society, 30, 1101-1106 (2009)). However, the recovery rate of the target was far below 1%, and there are still many problems to be solved for the practical use.

The present inventors have previously proposed a method (refolding method) for restoring a higher-order structure of a native state of a protein (denatured protein) which has lost its activity and/or stability as having become insoluble or lost a higher-order structure thereof (International Patent Application Publication No. WO2009/136568). According to this method, the protein structure can be effectively reconstructed by solubilizing a denatured and precipitated protein at pH 6.5 to 9.0 using a 1 to 3% predetermined aqueous solution of an acyl glutamic acid surfactant, and then lowering the concentration of the surfactant in the solubilized solution down to 0.02 to 0.5% using an arginine buffer.

SUMMARY OF THE INVENTION

Technical Problem

As described above, when a multivalent fusion protein is produced using a microorganism such as *Escherichia coli*, insoluble proteins are often formed in cells of the microorganism. In order to use the proteins as a pharmaceutical preparation or the like, refolding operations for reconstructing the active structure are required.

An aspect of the present invention is to provide a novel method for producing a multivalent fusion protein, particularly a multimeric protein containing an immunoglobulin fold structure in a subunit structure.

Solution to Problem

The present inventors have discovered that a fusion protein having an immunoglobulin fold structure, which has been solubilized with lauroyl-L-Glu, stably continues to be dissolved without forming a multimeric structure even if the concentration of lauroyl-L-Glu is lowered down to 0.02 to 0.5%. Furthermore, the inventors have discovered that while the fusion protein is being dissolved in the solution of lauroyl-L-Glu, only a subunit structure is formed, and so that when the solution is subsequently replaced with a specific buffer, a multimeric structure of the fusion protein can be formed.

Specifically, the present invention provides a method for producing a multimeric protein, which includes a monomeric protein obtained by fusing a protein having an immunoglobulin fold structure to a protein that can serve as a subunit structure, the method including the steps of:

(A) preparing a monomeric protein having an insoluble granular form in cells of a microorganism, the monomeric protein obtained by fusing a first protein having an immunoglobulin fold structure to a second different protein that can serve as a subunit structure;

(B) solubilizing the monomeric protein prepared in step (A) with an aqueous solution containing lauroyl glutamic acid or a salt thereof;

(C) diluting a solution obtained in step (B) in a buffer containing arginine or an arginine derivative to lower a concentration of the lauroyl glutamic acid or the salt thereof; and (D) replacing a solvent of a solution obtained in step (C) with a buffer using a method selected from the group consisting of (d1) column chromatography selected from the group consisting of gel filtration chromatography, ion-exchange chromatography, hydrophobic interaction chromatography, and a combination thereof;

(d2) ultrafiltration;

(d3) dialysis; and (d4) combinations thereof.

Advantageous Effects of Invention

The present invention makes it possible to produce a multivalent fusion protein of a multimeric structure having multiple affinity sites for a target antigen, by fusing a protein having an immunoglobulin fold structure to a different protein that can serve as a subunit structure, and utilizing the properties of the fusion protein to form the multimeric structure.

According to the present invention, it is possible to effectively form a multimeric structure even from a protein obtained by fusing two or more proteins having greatly different properties.

According to the method of the present invention, it is possible to prevent a protein that can serve as a subunit structure from aggregating and precipitating without forming a multimeric protein.

DESCRIPTION OF THE PREFERRED EMBODIMENTS

Figure 1:
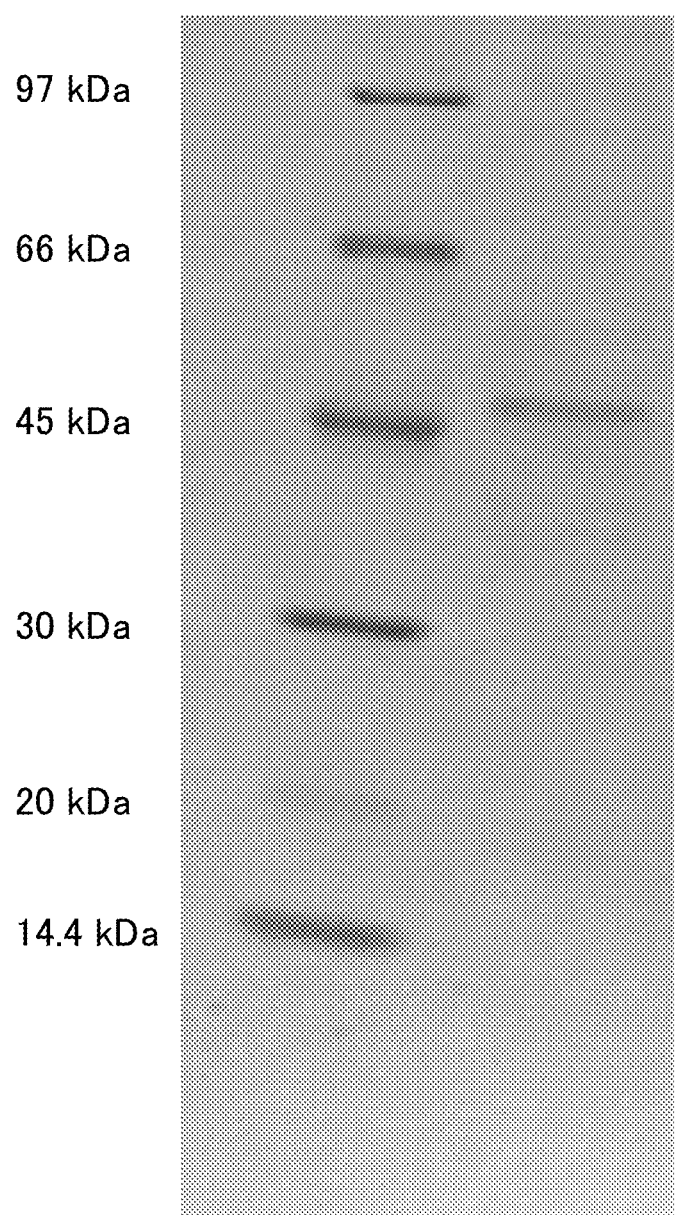
FIG. 1 shows the result of reducing SDS gel electrophoresis performed on HyHEL-10 scFv SA full length purified in Experiment 10.

Definitions:

The term "immunoglobulin fold structure" can refer to a stable domain structure of two β-structure planes linked by a disulfide bond. An immunoglobulin fold structure can serve as an affinity molecule that strongly binds to a specific molecule because of a loop structure present on the surface of the immunoglobulin fold structure. An immunoglobulin fold structure can also be called an immunoglobulin fold. Molecular Cell Biology, 3rd edition, page 1227, Tokyo Kagaku Dojin, 1997.

The term "subunit structure" can refer to structural units that assemble with each other by a non-covalent bond and form a protein having a stable multimeric structure. Molecular Cell Biology, 3rd edition, page 51, Tokyo Kagaku Dojin, 1997.

The term "multimeric structure (multimeric protein)" can refer to a high-order hierarchical structure which is formed by structural components, such as subunit structures, which are assembled via non-covalent bonds. The subunit structures are often regularly and symmetrically arranged. Molecular Cell Biology, 3rd edition, page 51, Tokyo Kagaku Dojin, 1997. A protein having a multimeric structure can be called a multimeric protein in some cases. Additionally, a structural component of a multimeric structure can also be called a monomeric protein.

Step (A): Preparation of Protein

A monomeric protein which is a structural component of a multimeric protein can be obtained by fusing a first protein having an immunoglobulin fold structure to a second protein that is different from the first protein and which serves as a subunit structure. The self-assembling and self-binding properties of this second protein make it possible to form a multimeric structure, and produce a multivalent fusion protein of a multimeric structure having multiple affinity sites for a target antigen.

The first protein having an immunoglobulin fold structure can include an anti-hen lysozyme antibody (for example, HyHEL-10, D1.3), an anti-TNFα antibody (infliximab, adalimumab, golimumab), an anti-HER2 antibody (trastuzumab), an anti-CD20 antibody (rituximab), an anti-VEGF antibody (bevacizumab), an anti-EGFR antibody (cetuximab, panitumumab), and the like.

The second protein that can serve as a subunit structure can include streptavidin, a human p53-derived tetrameric α-helix structure, a leucine zipper structure, functional fragments thereof, and the like. A functional fragment can refer to a protein fragment that can serve as a subunit structure, and an example thereof includes core streptavidin.

The monomeric protein can specifically include a fusion protein between scFv and streptavidin, and the like. More specifically, the monomeric protein can include a fusion protein between HyHEL-10 scFv and streptavidin, a fusion protein between D1.3 scFv and streptavidin, a fusion protein between HyHEL-10 scFv and core streptavidin, and the like.

The monomeric protein can have an insoluble granular form in cells of a microorganism. A "monomeric multimeric protein" can mean a protein having an insoluble granular form in cells of a microorganism, the protein obtained by fusing a protein having an immunoglobulin fold structure to a different protein that can serve as a subunit structure.

The monomeric protein can be produced by constructing a production system for the target monomeric protein according to methods known in the art, for example, methods described in Ueda et al, Gene. 1993, 129, 129-34, Lin, Y. et al, Cancer Res. 2006, 66, 3884-3892, Fischmann, T. O. et al, J. Biol. Chem. 1991, 266, 12915-12920, and Lin, Y. et al, Cancer Res. 2006, 66, 3884-3892, and subsequently culturing and collecting bacterial cells according to a conventional method.

Step (B): Solubilization of Monomeric Protein

Type of Surfactant

A surfactant can be used to solubilize the monomeric protein, such as lauroyl glutamic acid (lauroyl-Glu) or a salt thereof. The lauroyl-Glu may be in a D form, L form, or DL form. Lauroyl-L-Glu is a particular example.

Concentration of Surfactant

The lauroyl-Glu or the salt thereof can be used in the form of a 1 to 10% aqueous solution thereof, or a 1 to 8% aqueous solution thereof. Within these concentration ranges, it is possible to sufficiently increase the efficiency of solubilizing the monomeric protein while keeping a dilution rate in the next operation at an appropriate level.

pH

The pH of the aqueous solution at 25° C. can be selected to be a moderate condition of pH 6.5 to 9.0, or pH 7.0 to 8.8, in accordance with properties of the monomeric protein. The pH can be measured by a pH meter equipped with a pH electrode. The pH adjustment can be carried out using an alkali, such as sodium hydroxide. A buffer may be used as the aqueous solution.

Temperature and Time Period

From the lauroyl-Glu aqueous solution, a solution is obtained, in which the monomeric protein is solubilized. The monomeric protein may be added to the lauroyl-Glu aqueous solution, or the lauroyl-Glu aqueous solution may be added to the monomeric protein.

Then, the mixture can allowed to sit at 5 to 40° C., or at 15 to 40° C. These ranges are preferable so that cleavage of the monomeric protein due to a chemical reaction and modifications such as oxidation can be suppressed to the minimum.

The period of time for the mixture to be allowed to sit is normally 10 minutes to 3 hours, or 10 minutes to 1 hour. These ranges are preferable so that cleavage of the monomeric protein due to a chemical reaction and modifications such as oxidation can be suppressed to the minimum. The mixture may be stirred during this time period.

It can be confirmed whether the protein is solubilized or not, for example, by visual examination of turbidity, a UV absorption spectrum method at around 280 nm, or the like.

Step (C): Dilution with Arginine Buffer

Dilution Rate

Subsequently, the solution obtained in step (B), in which the monomeric protein is solubilized, can be diluted with a buffer containing arginine or an arginine derivative as an additive at a dilution rate of approximately several tens to 150, and maintained in situ until the monomeric protein is restored to a higher-order structure of the native state. The concentration of the lauroyl-Glu after the dilution can be 0.01 to 0.5%, or 0.02 to 0.3%. The dilution may be carried out in an appropriately-selected form of single stage, multi stage (step gradient), or linear gradient.

These ranges are preferable so that restoration of a higher-order structure of the native state can be facilitated and the stability of the monomeric protein can also be secured. It can be confirmed whether the monomeric protein has restored a higher-order structure of the native state, by spectrometry such as a CD spectrometry and a fluorescence spectrometry, a method, such as HPLC, in which physicochemical properties of the protein are observed, or using indicators of higher-order structure, such as enzymatic activity.

Type of Additives

Arginine used as the additive may have an L form or a D form. Arginine may form a salt with an inorganic acid, such as a hydrochloride salt, or a salt with an organic acid, such as acetate salt.

The arginine derivative includes arginines having an acyl group with 1 to 6 carbon atoms, such as acetylarginine, N-butyroyl arginine; agmatine with a carboxyl group removed; argininic acid with a hydroxyl group introduced in place of α-amino group; and the like. The arginine derivative can be acylated arginine, or N-butyroyl arginine.

Arginine hydrochloride is a particular example of the additive.

pH

As the buffer, sodium phosphate, sodium citrate, tris hydrochloride, or the like may be used. The pH should be suitable for the properties of the protein to be subjected to restoration of the native state, and is generally a neutral pH within pH 6.5 to 9.0. Accordingly, the pH in step (C) should be within this range, and may be different from the pH in step (B). The pH may be adjusted by using, for example, hydrochloric acid, sodium hydroxide, and/or the like.

Concentration of Additive

The concentration of the additive is selected each time in accordance with the properties of the protein to be subjected to restoration of the native state. The concentration of the additive is adjusted to make the concentration after the dilution 0.1 to 1.5 M, or 0.2 to 1.2 M. These ranges are preferable so that restoration of a higher-order structure of the native state can be facilitated.

Dilution Temperature and Maintenance Time

The dilution may be carried out at room temperature, or carried out at 5 to 10° C. if the heat stability of a target protein being restored its native state is not sufficiently high. The temperature adjustment may be carried out in an appropriately-selected form of single stage, multi stage (step gradient), or linear gradient.

After the dilution, the resulting solution may be maintained for a time period of several hours to several days. This time period can be 1 hour to 5 days, 1.5 hours to 3 days, or 2 hours to 24 hours. The dilution may be carried out gradually.

When the dilution is carried out in several stages, the concentration of the protein after dilution in the last stage is kept to 0.01 to 1.0 mg/ml, or 0.01 to 0.5 mg/ml, by condensation using an ultrafiltration membrane, for example,
after the dilution in the last stage in order to cancel out the dilution rate. When the target protein contains a Fab, such a protein concentration facilitates formation of disulfide bonds among heavy and light chains which make up the Fab.

Step (D): Replacement with Buffer

A solvent of a solution obtained in step (C) is replaced with a buffer. Thus, the lauroyl-Glu is removed from the system.

The replacement with the buffer is carried out using one or a combination of the following methods:

(d1) column chromatography, such as one or a combination of gel filtration chromatography, ion-exchange chromatography, hydrophobic interaction chromatography;

(d2) ultrafiltration;

(d3) dialysis. Among these, the column chromatography (d1) is preferable, and gel filtration chromatography is more preferable.

These operation methods are commonly used methods in the art, and those skilled in the art can select and determine the operation conditions as appropriate.

The chosen buffer can be a pH buffer. For example, it is possible to use one obtained by adding a strong acid (for example, hydrochloric acid, sulfuric acid, formic acid, or the like) in a calculated amount to a weakly basic solution, such as tris(hydroxymethyl)aminomethane, or one obtained by adding a dilute solution of a strong alkali (for example, sodium hydroxide, lithium hydroxide, or the like) in a calculated amount to a weakly acidic solution, such as phosphoric acid.

The buffer may contain arginine or an arginine derivative, or may contain an inorganic salt, such as NaCl, or a chelating agent, such as EDTA. In this case, the concentration is, for example, 0.001 to 1.2 M.

The pH of the buffer can be 6 to 9.

In the method, it can be confirmed whether the monomeric protein forms a multimeric protein by UV absorption, static light-scattering method, or the like.

Optional Step (i): Leaving Before Dilution with Additive Solution

Prior to the dilution with the arginine or arginine derivative buffer, some proteins may be mixed with a phosphate buffer solution or the like and left to sit. Specifically, between step (B) and step (C) described above, a phosphate buffer is added to make the concentration of the surfactant 2 to 5%, and thereafter left to sit at preferably 5 to 40° C. for preferably 10 minutes to 1 hour. Thereby, the percentage of the monomeric protein extracted is increased, and the solubility can be further increased. As a result, the percentage of restoration of a higher-order structure of the protein can be further increased. The pH of the solution thus obtained at 25° C. should be in a range from pH 6.5 to 9.0.

Optional Step (ii): Formation of Disulfide Bond

In some proteins, there may be a disulfide bond within a single molecule. It is preferable to facilitate formation of such disulfide bonds by a redox reaction of the proteins because the percentage of refolding is further improved.

The redox reaction may be carried out by adding a redox reagent which facilitates a thiol-disulfide exchange reaction and thereby allows formation of an intramolecular or intermolecular disulfide bond (for example, a mixture of oxidized glutathione (GSSG) and reduced glutathione (GSH), a mixture of cystine and cysteine, a mixture of cystamine and cysteamine, a mixture of oxidized glutathione or cystine and mercaptoethanol, or the like)), or a copper ion which facilitates air oxidation, or may be carried out by changing the redox potential of the protein. It is preferable to use a redox reagent.

The redox reaction may be carried out anytime after step (B) described above. For example, the redox reaction may be carried out in step (C) described above by adding a redox reagent together with an additive to the solution obtained in step (A), or may be carried out after the diluted solution is obtained in step (C) described above by adding a redox reagent to the diluted solution.

The concentration of the redox reagent or copper ion is adjusted to an appropriate concentration for each protein to be subjected to restoration of the native state.

The pH at 25° C. in this stage should be in a range from pH 6.5 to 9.0. The pH may be adjusted by using, for example, hydrochloric acid, sodium hydroxide, and/or the like.

The temperature of the solution may be in the same range as the temperature of the solution obtained in step (B) or in the same range as the temperature of the solution obtained in step (C). For the purpose of facilitating the redox reaction, approximately a temperature of 5 to 48° C. can be used.

After the redox reaction, the resultant may be left to sit at 5 to 48° C. for approximately 1 hour to 5 days (120 hours).

According to the method of the present invention, the percentage of refolding can be at least 10%, and reaches 30% in many cases.

Optional Step (iii): Purification

The protein which has restored the higher-order structure can be purified by a normal method, for example, ultrafiltration, dialysis, ion-exchange chromatography, gel filtration chromatography, hydrophobic interaction chromatography, reversed-phase chromatography, affinity chromatography, and the like.

The present inventors have reported in the previous application (International Patent Application Publication No. WO2009-136568) that a protein structure can be effectively reconstructed by solubilizing a denatured protein at pH 6.5 to 9.0 using a 1 to 3% predetermined acyl glutamic acid surfactant, and then diluting using an arginine buffer to lower the concentration of the surfactant down to 0.02 to 0.5%.

A multimeric protein has two or more subunits associated with each other by a non-covalent bond. Nevertheless, even if a multimeric protein is solubilized at a predetermined pH using a predetermined acyl glutamic acid surfactant (lauroyl-L-Glu) and then diluted with an arginine buffer, refolding cannot be completed only by these operations. Although not bound by any theory, it is assumed that lauroyl-L-Glu inhibits the association of the subunits.

The present invention takes advantage of this phenomenon. Although not bound by any theory, the present invention is based on the following assumption. Specifically, at first, only formation of a subunit structure is allowed to progress by inhibiting the association of subunits using lauroyl-L-Glu, and thereafter lauroyl-L-Glu considered to be a factor of inhibiting the association is replaced with a buffer and removed. As a result, the subunits are associated with each other, so that the refolding is completed.

Using the multimeric protein thus produced, therapeutic drugs, reagent for clinical tests, reagents for research, and so forth can be obtained against various diseases such as cancers, immune diseases, and lifestyle diseases. These pharmaceutical compositions may include an excipient, a carrier, or the like in addition to the multimeric protein obtained by the method of the present invention.

EXAMPLES

Reference Example 1

Preparation of Precipitate Containing Insoluble Granules of Full Length HyHEL-10 scFv SA A production system was constructed for producing a fusion protein (HyHEL-10 scFv SA full length) from a single-chain antibody fragment of variable region (HyHEL-10 scFv) and full length streptavidin (SA full length) using *Escherichia coli* BL21 strain (DE3) as a production host (Ueda et al, Gene. 1993, 129, 129-34, Lin, Y. et al, Cancer Res. 2006, 66, 3884-3892.).

Using a baffled conical flask, the production bacterium thus constructed was cultured according to an ordinary method in a 2×YT medium at 28° C. for 18 hours with shaking (4 L). HyHEL-10 scFv SA full length was accumulated in the form of insoluble granules in cells of *Escherichia coli*. The cells were collected, suspended in 20 mM tris hydrochloride and 0.5 M NaCl at pH 8.1, and broken by ultrasonic disintegration. The obtained suspension was subjected to centrifugation under conditions of 6000 g for 30 minutes to recover a precipitate containing insoluble granules of HyHEL-10 scFv SA full length.

The recovered precipitate was sequentially washed with a 2% Triton X-100 aqueous solution and acetone. Thereafter, Triton X-100 was completely removed by washing with purified water (Milli Q water). The centrifugation operation was performed under the above conditions again, and a precipitate containing the insoluble granules was obtained.

Aliquots, each 100 mg, of the obtained precipitate were put into four Eppendorf tubes. The tubes are referred to as tubes 1 to 4.

Note that, herein, unless otherwise specifically stated, the unit "%" means "mass %".

Reference Example 2

Preparation of Precipitate Containing Insoluble Granules of D1.3 scFv SA Full Length A precipitate containing insoluble granules of D1.3 scFv SA full length was obtained in the same manner as in Reference Example 1, except that a production system was constructed to produce a fusion protein (D1.3 scFv SA full length) of full length streptavidin (SA full length) and D1.3 scFv, which was used as a single-chain antibody fragment of variable region in place of HyHEL-10 scFv in Reference Example 1 (Fischmann, T. O. et al, J. Biol. Chem. 1991, 266, 12915-12920, Lin, Y. et al, Cancer Res. 2006, 66, 3884-3892.).

Experiment 1

(1) A 5% lauroyl-L-Glu solution (20 mM sodium phosphate, pH 8.5) was prepared.

(2) The precipitate in each of the tubes was solubilized by adding 0.2 ml of the solution into the tubes 1, 0.25 ml into the tube 2, 0.3 ml into the tube 3, and 0.35 ml into the tube 4. After placed in a vortex mixer at room temperature, the tubes 1 to 4 were gently centrifuged (10000 rpm, 1 minute) to remove formed foams.

(3) To each of the tubes, 20 mM sodium phosphate (pH 7) was added and filled to 0.5 ml. The final concentrations of lauroyl-L-Glu in the tubes 1 to 4 were adjusted to 2.0%, 2.5%, 3.0%, and 3.5%, respectively. After the pH in the tubes was adjusted to around 7.3 using a micro pH electrode, the tubes were heated at 37° C. for 30 minutes, and insoluble granules were extracted from the precipitate and dissolved. Note that, unless otherwise specifically stated, pH was measured at 25° C.

(4) Each of the obtained solutions was transferred to different Eppendorf tubes, and subjected to centrifugation at 14000 rpm (18700×g) for 10 minutes to recover supernatants 1 to 4.

(5) As a diluting solution, a 0.404 M arginine hydrochloride solution (1 mM EDTA, 80 mM tris hydrochloride, pH 7.2) was prepared.

(6) Using 7.425 ml of the diluting solution, 0.075 ml of each of the supernatants 1 to 4 recovered above was diluted at 5° C. Finally, 0.1% lauroyl-L-Glu and 0.4 M arginine hydrochloride (1 mM EDTA, 80 mM tris hydrochloride, pH 7.2, 7.5 ml) were prepared. The concentration of the protein was adjusted to 0.05 mg/ml.

(7) After being maintained at 5° C. for 18 hours, the diluted supernatants 1 to 4 were each concentrated 3 fold using a centrifugal ultrafiltration membrane (Amicon Ultra-15, NMWL of 10 kDa; manufactured by Millipore Corporation) and adjusted to 2.5 ml.

(8) Each of 2.5 ml of the 3-fold concentrated solutions was loaded onto a gel filtration column (PD-10 column, manufactured by GE Healthcare) equilibrated in advance with a buffer (50 mM tris hydrochloride, 0.2 M NaCl, 1 mM EDTA, pH 7.2), and subsequently deployed using 3.0 ml of the same buffer. Thereby, the total amount of the concentrated solution was recovered. Thus, the concentrated solution in the column was replaced with the buffer.

(9) After being maintained at 5° C. for 18 hours, these were subjected to centrifugation at 14000 rpm (18700×g) for 10 minutes. 30 μL of each of the resulting supernatants was subjected to gel filtration HPLC (column, Superdex 200 10/300 GL, manufactured by GE Healthcare; eluent, 0.1 M sodium phosphate, 0.8 M arginine hydrochloride, pH 6.8; detection method, UV absorption at 225 nm; quantification standard, a purified anti-von Willebrand factor monoclonal antibody (WO96/17078)) to quantify the amount of HyHEL-10 scFv SA full length having a tetrameric structure that formed. Table 1 shows the result.

| Lauroyl-L-Glu concentration (%) when insoluble granules were extracted | Amount (µg/ml) of tetrameric protein |
|---|---|
| 2.0 | 1.8 |
| 2.5 | 1.1 |
| 3.0 | 1.3 |
| 3.5 | 1.0 |

It was found that 1.0 to 1.8 µg/ml of the HyHEL-10 scFv SA full length multimeric protein can be recovered by solubilizing the precipitate using the 5.0% lauroyl-L-Glu solution, then extracting the fusion protein from the precipitate containing the insoluble granules and dissolving the insoluble granules using 2.0 to 3.5% of the lauroyl-L-Glu solution, followed by refolding.

Experiment 2

(1) A 2% lauroyl-L-Glu solution (20 mM sodium phosphate, pH 8.5) was prepared.

(2) The solution obtained in (1) was used and added to 100 mg of the precipitate obtained in Reference Example 1 to solubilize the precipitate in the same manner as in Experiment 1.

(3) A diluting solution containing arginine hydrochloride was prepared.

(4) The solution obtained in (2) was diluted 100 fold using the diluting solution prepared in (3). Finally, 30 ml of 0.02% lauroyl-L-Glu, 0.8 M arginine hydrochloride, 1 mM EDTA, 80 mM tris hydrochloride, 1 mM reduced glutathione, and 1 mM oxidized glutathione, was prepared with pH 8.0. The concentration of the protein was adjusted to 0.02 mg/ml.

(5) In the same manner as in Experiment 1, the solution obtained in (4) was maintained, then concentrated 3 fold using a centrifugal ultrafiltration membrane, and adjusted to 10 ml.

(6) After 40 µl of the 3-fold concentrated solution obtained in (5) was subjected to centrifugation at 14000 rpm (18700×g) for 10 minutes, 10 µl of the resulting supernatant was subjected to gel filtration HPLC in the same manner as in Experiment 1 to quantify HyHEL-10 scFv SA full length having a tetrameric structure formed.

(7) Independently, 2.5 ml of the 3-fold concentrated solution obtained in (5) was loaded onto a PD-10 column equilibrated in advance with a buffer (50 mM tris hydrochloride, 0.2 M arginine hydrochloride, 1 mM EDTA, pH 6.6), and subsequently deployed using 3.0 ml of the same buffer. Thereby, the total amount of the concentrated solution was recovered.

(8) After the recovered product in (7) was maintained and centrifuged in the same manner as in Experiment 1, 12 µl of the resulting supernatant was similarly subjected to the gel filtration HPLC to quantify the amount of HyHEL-10 scFv SA full length having a tetrameric structure that formed. Table 2 shows the result.

| Step | Amount (µg/ml) of tetrameric protein |
|---|---|
| After solubilized solution was diluted | 0 |
| After diluted solution was replaced with buffer | 2.4 |

The result shown in Table 2 revealed that no HyHEL-10 scFv SA full length multimeric protein was detected at all in the stage of diluting 100 fold using the diluting solution (step (4)), but that 2.4 µg/ml of the HyHEL-10 scFv SA full length multimeric protein can be recovered by replacing with the buffer and maintaining the resultant (steps (7) and (8)).

Experiment 3

(1) In the same manner as in Experiment 1, 100 mg of the precipitate obtained in Reference Example 1 was solubilized.

(2) Aliquots, each 0.15 ml, of the solution were diluted 100 fold with the diluting solution in the same manner as in Experiment 1. Finally, the pH was adjusted to 7.2 or 8.4 (0.05% lauroyl-L-Glu, 0.8 M arginine hydrochloride, 1 mM EDTA, 80 mM tris hydrochloride, 15 ml). The concentration of the protein was adjusted to 0.05 mg/ml.

(3) In the same manner as in Experiment 1, each of the solutions obtained in (2) was maintained, then concentrated 3 fold in concentration using a centrifugal ultrafiltration membrane, and adjusted to 5 ml.

(4) Each 2.5-ml aliquot of the resultant was loaded onto a PD-10 column using the same buffer as that in Experiment 1, and subsequently deployed using 3.0 ml of the same buffer. Thereby, the total amount of the concentrated solution was recovered.

(5) In the same manner as in Experiment 1, this was maintained, centrifuged, and then subjected to gel filtration HPLC to quantify the amount of HyHEL-10 scFv SA full length having a tetrameric structure that formed.

| pH after dilution | Amount (µg/ml) of tetrameric protein |
|---|---|
| 7.2 | 1.8 |
| 8.4 | 1.5 |

The result shown in Table 3 revealed that approximately the same amounts of HyHEL-10 scFv SA full length multimeric proteins can be recovered even by diluting to pH 7.2 or 8.4 after the solubilization.

Experiment 4

(1) In the same manner as in Experiment 1, 100 mg of the precipitate obtained in Reference Example 1 was solubilized.

(2) Dilute solutions containing arginine hydrochloride at various concentrations were prepared.

(3) Aliquots, each 0.075 ml, of the solution obtained in (1) were sorted and diluted 100 fold with the diluting solutions prepared in (2). The final concentration of lauroyl-L-Glu was 0.02%, 0.05%, 0.07%, 0.1%, 0.2%, or 0.3% (0.8 M arginine hydrochloride, 1 mM EDTA, pH 7.2, 7.5 ml). The concentration of the protein was adjusted to 0.05 mg/ml.

(4) In the same manner as in Experiment 1, each of the solutions obtained in (3) was maintained, then concentrated 3 fold in concentration using a centrifugal ultrafiltration membrane, and adjusted to 2.5 ml.

(5) Each 2.5 ml of the 3-fold concentrated solutions obtained in (4) was loaded onto a PD-10 column using the same buffer as that in Experiment 1, and subsequently deployed using 3.0 ml of the same buffer. Thereby, the total amount of the concentrated solution was recovered.

(6) In the same manner as in Experiment 1, this was maintained, centrifuged, and then subjected to gel filtration HPLC to quantify the amount of HyHEL-10 scFv SA full length having a tetrameric structure that formed.

| Lauroyl-L-Glu concentration (%) after dilution | Amount (µg/ml) of tetrameric protein |
| --- | --- |
| 0.02 | 0.9 |
| 0.05 | 1.5 |
| 0.07 | 1.0 |
| 0.10 | 1.4 |
| 0.20 | 1.4 |
| 0.30 | 1.0 |

The result shown in Table 4 revealed that approximately the same amounts of HyHEL-10 scFv SA full length multimeric proteins can be recovered by diluting to make the concentration of lauroyl-L-Glu 0.02 to 0.30% after the solubilization.

Experiment 5

(1) In the same manner as in Experiment 1, 100 mg of the precipitate obtained in Reference Example 1 was solubilized.

(2) Diluting solutions containing arginine hydrochloride at various concentrations were prepared.

(3) Aliquots, each 0.075 ml, of the solution obtained in (1) were sorted and diluted 100 fold with the diluting solutions prepared in (2). The final concentration of arginine hydrochloride was 0.4 M, 0.8 M, 1.0 M, or 1.2 M (0.025% lauroyl-L-Glu, 1 mM EDTA, 80 mM tris hydrochloride, pH 7.2, 7.5 ml). The concentration of the protein was adjusted to 0.05 mg/ml.

(4) In the same manner as in Experiment 1, each of the solutions obtained in (3) was maintained, then concentrated 3 fold in concentration using a centrifugal ultrafiltration membrane, and adjusted to 2.5 ml.

(5) Each 2.5 ml of the 3-fold concentrated solutions obtained in (4) was loaded onto a PD-10 column using the same buffer as that in Experiment 1, and subsequently deployed using 3.0 ml of the same buffer. Thereby, the total amount of the concentrated solution was recovered.

(6) In the same manner as in Experiment 1, this was maintained, centrifuged, and then subjected to gel filtration HPLC to quantify the amount of HyHEL-10 scFv SA full length having a tetrameric structure that formed.

| Arginine concentration (M) after dilution | Amount (µg/ml) of tetrameric protein |
| --- | --- |
| 0.4 | 1.1 |
| 0.8 | 1.3 |
| 1.0 | 1.1 |
| 1.2 | 0.7 |

It was found that approximately the same amounts of HyHEL-10 scFv SA full length multimeric proteins can be recovered by diluting to make the concentration of arginine hydrochloride 0.4 to 1.2 M after the solubilization.

Experiment 6

(1) In the same manner as in Experiment 1, 100 mg of the precipitate obtained in Reference Example 1 was solubilized.

(2) Dilute solutions containing arginine hydrochloride with reduced glutathione and oxidized glutathione having variously changed concentrations were prepared.

(3) Aliquots, each 0.075 ml, of the solution obtained in (1) were sorted and diluted 100 fold with the diluting solutions prepared in (2). The final concentrations of reduced glutathione and oxidized glutathione varied from none to 5 mM (0.05% lauroyl-L-Glu, 1.2 M arginine hydrochloride, 1 mM EDTA, 80 mM tris hydrochloride, pH 8.4, 7.5 ml). The concentration of the protein was adjusted to 0.05 mg/ml.

(4) In the same manner as in Experiment 1, each of the solutions obtained in (3) was maintained, then concentrated 3 fold in concentration using a centrifugal ultrafiltration membrane, and adjusted to 2.5 ml.

(5) Each 2.5 ml of the 3-fold concentrated solutions obtained in (4) was loaded onto a PD-10 column equilibrated in advance with a buffer (50 mM tris hydrochloride, 0.4 M arginine hydrochloride, 1 mM EDTA, pH 8.0), and subsequently deployed using 3.0 ml of the same buffer. Thereby, the total amount of the concentrated solution was recovered.

(6) In the same manner as in Experiment 1, this was maintained, centrifuged, and then subjected to gel filtration HPLC to quantify the amount of HyHEL-10 scFv SA full length having a tetrameric structure that formed.

| Reduced glutathione concentration (mM) after dilution | Oxidized glutathione concentration (mM) after dilution | Amount (µg/ml) of tetrameric protein |
| --- | --- | --- |
| not added | not added | 2.2 |
| 5 | 1 | 2.5 |
| 1 | 1 | 1.7 |
| 1 | 5 | 1.4 |

It was found that HyHEL-10 scFv SA full length having a tetrameric structure formed can be recovered even if the concentrations of reduced glutathione and oxidized glutathione vary from none to 5 mM. This revealed that when a specific combination of reduced and oxidized glutathione concentrations is necessary depending on a protein, an optimal concentration combination can be selected as appropriate.

Experiment 7

(1) In the same manner as in Experiment 2, 100 mg of the precipitate obtained in Reference Example 1 was solubilized.

(2) A diluting solution containing arginine hydrochloride was prepared.

(3) Aliquots, each 0.3 ml, of the solution obtained in (1) were sorted and diluted with the above diluting solution. Finally, 30 ml of 0.02% lauroyl-L-Glu, 0.8 M arginine hydrochloride, 1 mM EDTA, 1 mM reduced glutathione, 1 mM oxidized glutathione, and 80 mM tris hydrochloride, was prepared with pH 8.0. The concentration of the protein was adjusted to 0.02 mg/ml.

(4) In the same manner as in Experiment 1, the solution obtained in (3) was maintained, then concentrated 3 fold in concentration using a centrifugal ultrafiltration membrane, and adjusted to 10 ml.

(5) Four types of buffers were prepared in total, which contained 0.2 M NaCl or arginine hydrochloride in addition to 50 mM tris hydrochloride and 1 mM EDTA and had pH 6.6 or pH 7.6.

(6) Each 2.5-ml aliquot of the 3-fold concentrated solution obtained in (4) was loaded onto a PD-10 column equilibrated in advance with any one of the above buffers, and subsequently deployed using 3.0 ml of the same buffer. Thereby, the total amount of the concentrated solution was recovered.

(7) In the same manner as in Experiment 1, this was maintained, centrifuged, and then subjected to gel filtration HPLC to quantify HyHEL-10 scFv SA full length having a tetrameric structure formed.

| Salt added to buffer (0.2M added) | pH of buffer | Amount (µg/ml) of tetrameric protein |
| --- | --- | --- |
| NaCl | 6.6 | 0.3 |
| NaCl | 7.6 | 1.0 |
| arginine hydrochloride | 6.6 | 2.4 |
| arginine hydrochloride | 7.6 | 2.8 |

Whether the salt added to the buffer was NaCl or arginine hydrochloride, the HyHEL-10 scFv SA full length multimeric proteins were successfully recovered. It was found that when arginine hydrochloride is used as a salt to be added, the amount of a tetrameric protein recovered is increased in comparison with when NaCl is used. It was found that when NaCl is used as a salt to be added, the recovery amount is increased if the pH is increased from 6.6 to 7.6.

Experiment 8

(1) In the same manner as in Experiment 2, 100 mg of the precipitate obtained in Reference Example 1 was solubilized.

(2) A diluting solution containing arginine hydrochloride was prepared.

(3) Then, 0.45 ml of the solution obtained in (1) was diluted 100 fold with the above diluting solution. Finally, 45 ml of 0.02% lauroyl-L-Glu, 0.8 M arginine hydrochloride, 1 mM EDTA, and 80 mM tris hydrochloride was prepared, with pH 8.0. The concentration of the protein was adjusted to 0.05 mg/ml.

(4) In the same manner as in Experiment 1, the solution obtained in (3) was maintained, then concentrated 3 fold in concentration using a centrifugal ultrafiltration membrane, and adjusted to 15 ml.

(5) Three types of buffers were prepared in total, which respectively had pH 6.5, pH 7.2, and pH 8.4. Nevertheless, the buffer having pH 6.5 contained 0.2 M arginine hydrochloride, 1 mM EDTA, and 25 mM sodium phosphate. The buffers having pH 7.2 and pH 8.4 contained 50 mM tris hydrochloride in place of 25 mM sodium phosphate.

(6) Each 2.5-ml aliquot of the 3-fold concentrated solution obtained in (4) was loaded onto a PD-10 column equilibrated in advance with any one of the above buffers, and subsequently deployed using 3.0 ml of the same buffer. Thereby, the total amount of the concentrated solution was recovered.

(7) In the same manner as in Experiment 1, this was maintained, centrifuged, and then subjected to gel filtration HPLC to quantify the amount of HyHEL-10 scFv SA full length having a tetrameric structure that formed.

| pH of buffer | Amount (µg/ml) of tetrameric protein |
| --- | --- |
| 6.5 | 1.8 |
| 7.2 | 1.5 |
| 8.4 | 1.1 |

It was found that HyHEL-10 scFv SA full length multimeric proteins can be recovered by setting the pH of the buffer at 6.5 to 8.4.

Experiment 9

(1) In the same manner as in Experiment 2, 100 mg of the precipitate obtained in Reference Example 1 was solubilized.

(2) A diluting solution containing arginine hydrochloride was prepared.

(3) Then, 0.45 ml of the solution obtained in (1) was diluted 100 fold with the above diluting solution. Finally, 45 ml of 0.02% lauroyl-L-Glu, 0.8 M arginine hydrochloride, 1 mM EDTA, 1 mM reduced glutathione, 1 mM oxidized glutathione, and 80 mM tris hydrochloride was prepared, with pH 8.0. The concentration of the protein was adjusted to 0.02 mg/ml.

(4) In the same manner as in Experiment 1, the solution obtained in (3) was maintained, then concentrated 3 fold in concentration using a centrifugal ultrafiltration membrane, and adjusted to 15 ml.

(5) Six types of buffers were prepared in total, in which the concentration of arginine hydrochloride varied: 0.05 M, 0.1 M, 0.2 M, 0.4 M, and 0.8 M. Nevertheless, all of the buffers had 25 mM sodium phosphate and 1 mM EDTA, pH 6.6.

(6) Each 2.5-ml aliquot of the 3-fold concentrated solution obtained in (4) was loaded onto a PD-10 column equilibrated in advance with any one of the above buffers, and subsequently deployed using 3.0 ml of the same buffer. Thereby, the total amount of the concentrated solution was recovered.

(7) After maintained at 5° C. for 18 hours, this was concentrated 5 fold in concentration using a centrifugal ultrafiltration membrane (Amicon Ultra-4, NMWL of 10 kDa) and adjusted to 0.6 ml.

(8) Of this, 0.5 ml was loaded onto PD MiniTrap G-25 (manufactured by GE Healthcare) equilibrated in advance with a buffer (50 mM tris hydrochloride, 0.2 M NaCl, 1 mM EDTA, pH 8.0), and deployed using 0.9 ml of the same buffer. Thereby, the total amount was recovered.

(9) Further, the resultant was loaded onto an anion exchange column (HiTrap Q HP; manufactured by GE Healthcare) equilibrated in advance with the same buffer as that used in (8). The total amount of a fraction having flowed through the column was recovered. In this manner, the aggregate was removed.

(10) The flow-through fraction was concentrated to 0.5 ml using an ultrafiltration membrane (Amicon Ultra-4, NMWL of 10 kDa), and subjected to centrifugation at 14000 rpm (18700×g) for 10 minutes. Then, 30 µl of the resulting supernatant was subjected to gel filtration HPLC to quantify the amount of HyHEL-10 scFv SA full length having a tetrameric structure that formed.

| Arginine concentration (M) in buffer | Amount (µg/ml) of tetrameric protein |
| --- | --- |
| 0.05 | 0.7 |
| 0.1 | 2.4 |

-continued

| Arginine concentration (M) in buffer | Amount (μg/ml) of tetrameric protein |
|---|---|
| 0.2 | 6.2 |
| 0.4 | 5.1 |
| 0.8 | 4.9 |

It was found that a HyHEL-10 scFv SA full length multimeric protein is recovered by setting the concentration of arginine hydrochloride added to the buffer at 0.05 to 0.8 M. It was found that the recovery amount is high when the concentration of arginine hydrochloride added is 0.2 to 0.8 M.

Experiment 10

(1) In the same manner as in Experiment 2, 100 mg of the precipitate obtained in Reference Example 1 was solubilized.

(2) A diluting solution containing arginine hydrochloride was prepared.

(3) Then, 3.8 ml of the solution obtained in (1) was diluted 100 fold with the above diluting solution. Finally, 380 ml of 0.02% lauroyl-L-Glu, 0.8 M arginine hydrochloride, 1 mM EDTA, 1 mM reduced glutathione, 1 mM oxidized glutathione, and 80 mM tris hydrochloride was prepared, with pH 8.0. The concentration of the protein was adjusted to 0.02 mg/ml.

(4) After being maintained at 5° C. for 18 hours, the solution obtained in (3) was concentrated to 75 ml using an ultrafiltration membrane (Pellicon 3, NMWL of 10 kDa; manufactured by Millipore Corporation).

(5) The resultant was loaded separately three times, each 25 ml, onto a Sephadex G-25 column (5 cmφ×6.5 cm; manufactured by GE Healthcare) equilibrated in advance with a buffer (25 mM sodium phosphate, 0.1 M arginine hydrochloride, 1 mM EDTA, pH 6.6), and subsequently deployed using the same buffer. Thereby, a protein fraction was obtained using UV absorption at 280 nm as an indicator.

(6) After the obtained protein fraction was maintained at 5° C. for 18 hours, a total of 105 ml thereof was concentrated approximately 3 fold in concentration to 36 ml using an ultrafiltration membrane (Pellicon XL, regenerated cellulose membrane, NMWL of 10 kDa; manufactured by Millipore Corporation).

(7) This was loaded separately three times, each 12 ml, onto Superdex 200 pg 26/60 (2.6 cmφ×60 cm; manufactured by GE Healthcare) equilibrated in advance with a buffer (50 mM tris hydrochloride, 0.2 M NaCl, 1 mM EDTA, pH 8.0), and a HyHEL-10 scFv SA full length fraction was recovered using UV absorption at 280 nm as an indicator.

(8) After the fractions were combined, quantification by gel filtration HPLC confirmed 920 μg of the HyHEL-10 scFv SA full length multimeric protein. This fraction was concentrated to 10 ml using an ultrafiltration membrane (Amicon Ultra-15, NMWL of 30 kDa).

(9) In order to remove an aggregate contained therein, the fraction was loaded onto an anion exchange column (HiTrap CaptoQ, 5 ml; manufactured by GE Healthcare) equilibrated in advance with the same buffer as that used in (7) to thereby recover the total amount of a fraction having flowed through the column from which the aggregate was removed. Quantification by gel filtration HPLC confirmed 450 μg of the HyHEL-10 scFv SA full length multimeric protein.

(10) After condensation to 2.5 ml, the total amount was loaded onto Superdex 200 pg 16/60 (1.6 cmφ×60 cm; manufactured by GE Healthcare) equilibrated in advance with a buffer (50 mM tris hydrochloride, 0.2 M NaCl, 1 mM EDTA, pH 8.0), and the HyHEL-10 scFv SA full length multimeric protein was recovered using UV absorption at 280 nm as an indicator. Quantification by gel filtration HPLC confirmed 150 μg of the HyHEL-10 scFv SA full length multimeric protein.

Figure 2:
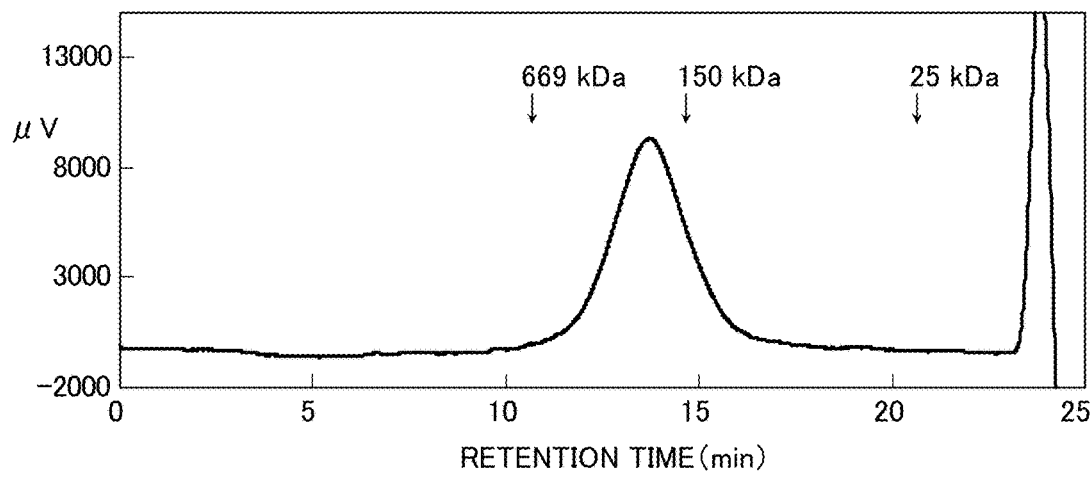
FIG. 2 is a graph showing a gel filtration HPLC pattern (UV absorption at 225 nm) of the HyHEL-10 scFv SA full length purified in Experiment 10.

(11) The purified HyHEL-10 scFv SA full length multimeric protein showed a single band around 45 kDa in reducing SDS gel electrophoresis (FIG. 1), and showed a single peak at a molecular weight of 230 kDa in gel filtration HPLC. This revealed that a tetramer was formed as expected (FIG. 2).

(12) The inhibitory activity of the purified HyHEL-10 scFv SA full length on an egg white lysozyme was examined according to a published report (Ueda et al, Gene. 1993, 129, 129-34.).

As a buffer for measurement, a 50 mM phosphoric acid solution (pH 6.2) with 200 mM NaCl was used. The final concentration of a hen egg white lysozyme (Seikagaku Corporation Code No. 100940) was adjusted to 1.5 μM, and a mixture solution was prepared in such a manner that the relative concentration between the HyHEL-10 scFv SA full length multimeric protein and the lysozyme was [HyHEL-10 scFv SA full length multimeric protein]/[lysozyme]=0 to 2.0. After this was heated at 28° C. for 1 hour, 30 μl thereof was mixed with 970 μl of a microbial suspension (*Micrococcus lysodeiktius* ATCC No. 4698; M3770-5G, manufactured by Sigma-Aldrich Corporation) adjusted to have an absorbance of 1.0 at 540 nm. Immediately thereafter, a change in the absorbance was measured for 5 minutes at a measurement wavelength of 540 nm.

It was found that as the amount of the HyHEL-10 scFv SA full length added is increased, the lytic activity against a microorganism by the hen egg white lysozyme is significantly inhibited, and that the purified HyHEL-10 scFv SA full length multimeric protein has a lysozyme inhibitory activity.

Experiment 11

(1) The same solubilization treatment as in Experiment 1 was carried out on 570 mg of the precipitate containing insoluble granules of D1.3 scFv SA full length obtained in Reference Example 2. Finally, 1.8 ml of a 2% lauroyl-L-Glu solution was obtained.

(2) This solution was diluted 100 fold with a diluting solution. Finally, 180 ml of 0.02% lauroyl-L-Glu, 0.8 M arginine hydrochloride, 1 mM EDTA, 1 mM reduced glutathione, 1 mM oxidized glutathione, and 80 mM tris hydrochloride was prepared, with pH 8.0. The concentration of the protein was adjusted to 0.05 mg/ml.

(3) After being maintained at 5° C. for 18 hours, the resultant was concentrated to 50 ml using an ultrafiltration membrane (Pellicon 3, NMWL of 10 kDa; manufactured by Millipore Corporation).

(4) This was loaded separately twice, each 25 ml, onto a Sephadex G-25 column (5 cmφ×6.5 cm; manufactured by GE Healthcare) equilibrated in advance with a buffer (25 mM sodium phosphate, 0.2 M arginine hydrochloride, 1 mM EDTA, pH 6.6), and subsequently deployed using the same buffer. Thereby, a protein fraction was obtained using UV absorption at 280 nm as an indicator.

(5) After the obtained protein fraction was maintained at 5° C. for 18 hours, a total of 70 ml thereof was concentrated approximately 3 fold in concentration to 24 ml using an ultrafiltration membrane (Pellicon XL, regenerated cellulose membrane, NMWL of 10 kDa; manufactured by Millipore Corporation).

(6) This was loaded separately twice, each 12 ml, onto Superdex 200 pg 26/60 (2.6 cmφ×60 cm; manufactured by GE Healthcare) equilibrated in advance with a buffer (50 mM tris hydrochloride, 0.2 M NaCl, 1 mM EDTA, pH 8.0), and a D1.3 scFv SA full length fraction was recovered using UV absorption at 280 nm as an indicator.

(7) The fraction was concentrated to 6 ml using an ultrafiltration membrane (Amicon Ultra-15, NMWL of 30 kDa). The resultant was loaded onto an anion exchange column (HiTrap Capto Q, 5 ml; manufactured by GE Healthcare) equilibrated in advance with the same buffer as that used in (6) to recover the total amount of a fraction having flowed through the column from which the aggregate was removed. Quantification by gel filtration HPLC confirmed 220 µg of the D1.3 scFv SA full length multimeric protein.

(8) After condensation to 2.0 ml, the total amount was loaded onto Superdex 200 pg 16/60 (1.6 cmφ×60 cm; manufactured by GE Healthcare) equilibrated in advance with a buffer (50 mM tris hydrochloride, 0.2 M NaCl, 1 mM EDTA, pH 8.0), and the D1.3 scFv SA full length multimeric protein was recovered using UV absorption at 280 nm as an indicator. Quantification by gel filtration HPLC confirmed 64 µg of the purified D1.3 scFv SA full length.

Figure 3:
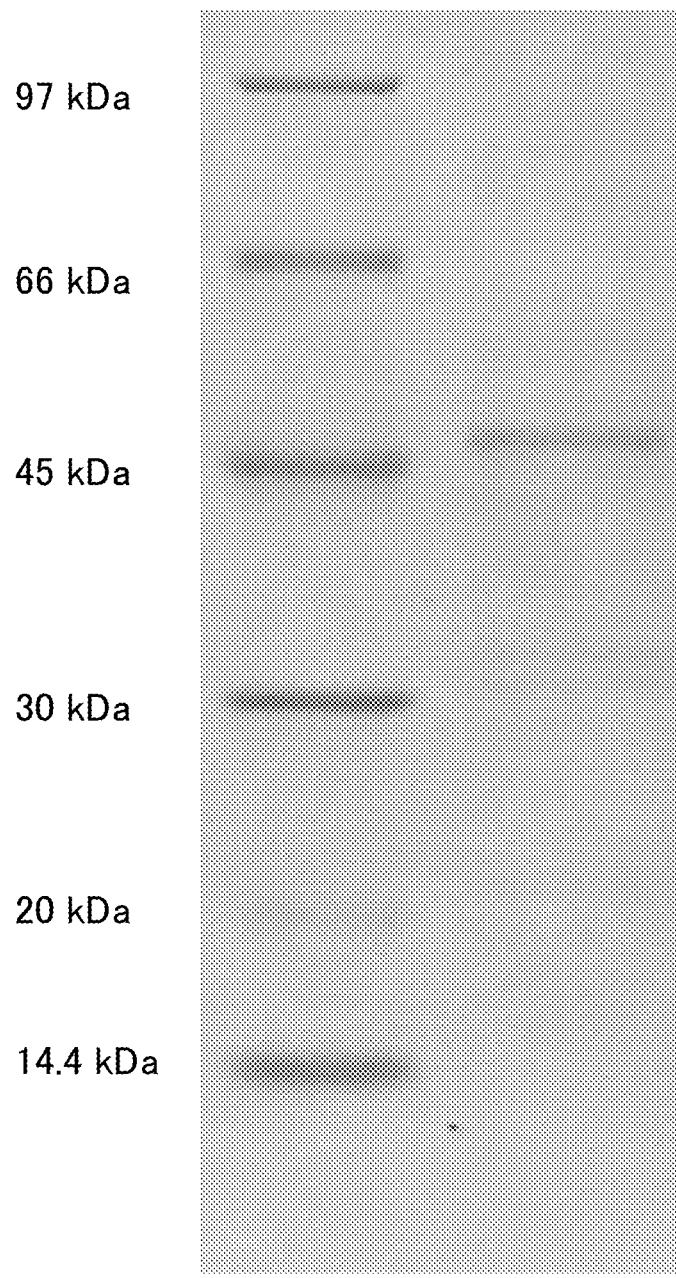
FIG. 3 shows the result of reducing SDS gel electrophoresis performed on D1.3 scFv SA full length purified in Experiment 11.
Figure 4:
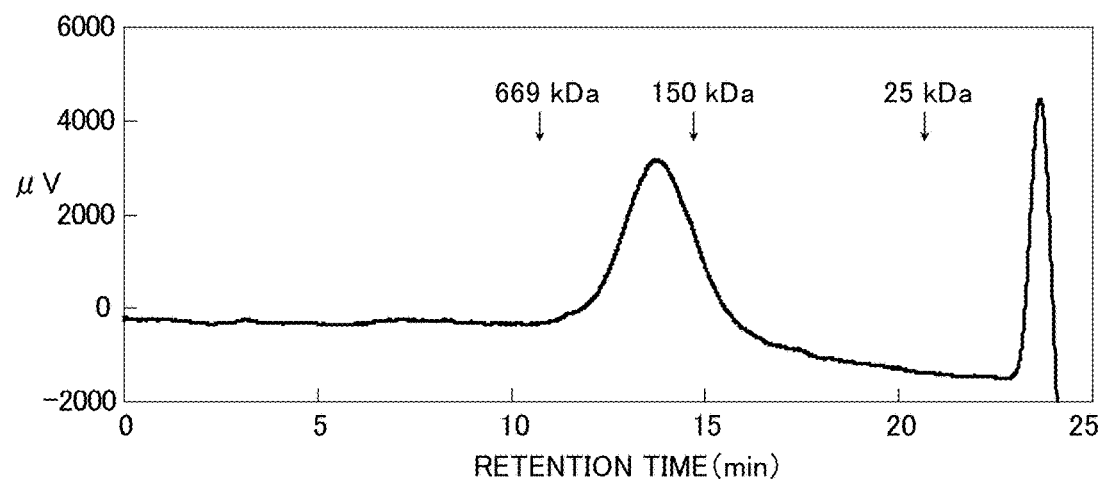
FIG. 4 is a graph showing a gel filtration HPLC pattern (UV absorption at 225 nm) of the D1.3 scFv SA full length purified in Experiment 11.

(9) The purified D1.3 scFv SA full length multimeric protein showed a single band around 45 kDa in reducing SDS gel electrophoresis (FIG. 3), and showed a single peak at 200 kDa in gel filtration HPLC. This revealed that a tetramer was formed as expected (FIG. 4).

(10) The result of subjecting the purified D1.3 scFv SA full length multimeric protein obtained in (8) to the same enzyme inhibition evaluation as in Experiment 10 revealed that the multimeric protein has an inhibitory activity on an egg white lysozyme.

Comparative Experiment Example 1

(1) A solution of 8 M guanidine hydrochloride and 20 mM sodium phosphate having pH 8.5 was prepared.

(2) To 100 mg of the precipitate containing insoluble granules obtained in Reference Example 1, 0.375 ml of the above solution was added to solubilize the precipitate. After being placed in a vortex mixer at room temperature, the resultant was gently centrifuged to remove formed foams.

(3) To this, a small amount of 20 mM sodium phosphate at pH 8.5 was added and adjusted to 0.5 ml. The mixture was heated at 37° C. for 30 minutes and placed in a vortex mixer. Then, it was confirmed that the insoluble granules were sufficiently dissolved.

(4) The resulting solution was subjected to centrifugation at 14000 rpm (18700×g) for 10 minutes, and 0.25 ml of a supernatant was recovered.

(5) Then, 0.05 ml of the supernatant was diluted 100 fold with a diluting solution. Finally, prepared was 5 ml of 6 M guanidine hydrochloride, 0.2 M NaCl, 50 mM tris hydrochloride, and 1 mM EDTA, with pH 8.0. The concentration of the protein was adjusted to 0.02 mg/ml.

(6) This was subjected to stepwise dialysis (Tsumoto et al, Journal of Immunological Methods, 219, 119-129 (1998)). Specifically, the dialysis was carried out at 5° C. for a predetermined period with 1000 ml of dialysis buffers denoted by dialysis numbers 1 to 5 shown in Table 10. Finally, 5.5 ml of a dialyzed fraction was recovered. After the recovered dialyzed fraction was subjected to centrifugation at 14000 rpm (18700×g) for 10 minutes, 30 µl of the resulting supernatant was subjected to gel filtration HPLC to quantify HyHEL-10 scFv SA full length having a tetrameric structure formed. As a result, no peak of the HyHEL-10 scFv SA full multimeric protein was confirmed (not shown).

| Dialysis number | Guanidine hydrochloride concentration (M) | NaCl concentration (M) | Arginine concentration (M) | Tris hydrochloride concentration (M) | EDTA concentration (mM) | pH | Dialysis period |
|---|---|---|---|---|---|---|---|
| 1 | 3.0 | 0.2 | 0 | 0.05 | 1 | 8.0 | 9 h |
| 2 | 2.0 | 0.2 | 0 | 0.05 | 1 | 8.0 | 14 h |
| 3 | 1.0 | 0.2 | 0.4 | 0.05 | 1 | 8.0 | 11 h |
| 4 | 0.5 | 0.2 | 0 | 0.05 | 1 | 8.0 | 16 h |
| 5 | 0 | 0.2 | 0 | 0.05 | 1 | 8.0 | 25 h |

Comparative Experiment Example 2

(1) A solution of 8 M guanidine hydrochloride, 20 mM sodium phosphate having pH 8.5 was prepared.

(2) To 100 mg of the precipitate containing insoluble granules obtained in Reference Example 1, 0.375 ml of the above solution was added to solubilize the precipitate. After being placed in a vortex mixer at room temperature, the resultant was gently centrifuged to remove formed foams.

(3) To this, a small amount of 20 mM sodium phosphate at pH 8.5 was added and adjusted to 0.5 ml. The mixture was heated at 37° C. for 30 minutes and placed in a vortex mixer. Then, it was confirmed that the insoluble granules were sufficiently dissolved.

(4) The resulting solution was subjected to centrifugation at 14000 rpm (18700×g) for 10 minutes, and 0.32 ml of a supernatant was recovered.

(5) As a diluting solution, four types of diluting solutions were prepared in total, in which lauroyl-L-Glu was either added or not added, and reduced and oxidized glutathiones were either added or not added. Nevertheless, all of the diluting solutions had 0.06 M guanidine hydrochloride, 0.2 M arginine hydrochloride, 80 mM tris hydrochloride, and 1 mM EDTA, with pH 7.2.

(6) Aliquots, each 0.075 ml, of the supernatant obtained in (4) were diluted 100 fold with the diluting solutions. Finally, each was prepared to be 7.5 ml of 0.06 M guanidine hydrochloride, 0.2 M arginine hydrochloride, 80 mM tris hydrochloride, and 1 mM EDTA, with pH 7.2. Nevertheless, finally, four types in total were adjusted to have a lauroyl-L-Glu concentration of 0% or 0.05% and reduced and oxidized glutathione concentrations of 0 mM or 1 mM. The concentration of the protein was adjusted to 0.05 mg/ml.

(7) In the same manner as in Experiment 1, each of the solutions obtained in (6) was maintained, then concentrated 3 fold in concentration using a centrifugal ultrafiltration membrane, and adjusted to 2.5 ml.

(8) Each of these was loaded onto a PD-10 column equilibrated in advance with a buffer (50 mM tris hydrochloride, 0.2 M NaCl, 1 mM EDTA, pH 7.2), and subsequently deployed using 3.0 ml of the same buffer. Thereby, the total amount of the concentrated solution was recovered.

After maintained at 5° C. for 18 hours, this was subjected to centrifugation at 14000 rpm (18700×g) for 10 minutes, and 30 µl of the resulting supernatant was similarly subjected to gel filtration HPLC to quantify the amount of HyHEL-10 scFv SA full length having a tetrameric structure that formed.

(9) As a result, when the insoluble granules were solubilized using a protein denaturing agent (guanidine hydrochloride) in place of lauroyl-L-Glu, no peak of the HyHEL-10 scFv SA full length multimeric protein was confirmed at all (not shown). Even when lauroyl-L-Glu or glutathione was added in the diluting solution, the recovery rate of the HyHEL-10 scFv SA full length multimeric protein was not increased (not shown).

Reference Example 3

Preparation of Precipitate Containing Insoluble Granules of HyHEL-10 scFv SAcore In the same manner as in Reference Example 1, a production system was constructed for a fusion protein (HyHEL-10 scFv SAcore) between a single-chain antibody fragment of variable region (HyHEL-10 scFv) and naturally occurring wildtype core streptavidin (natural core Streptavidin) using an *Escherichia coli* BL21 strain (DE3) as a production host. The amino acid sequencing of the natural core Streptavidin followed a published report (Takeshi Sano, et al. The Journal of Biological Chemistry 270, 47, 28204-28209 (1995).

Using a culture flask, the production bacterium thus constructed was cultured according to an ordinary method in an LB medium at 37° C. with shaking. The absorbance at 660 nm after culturing for several hours was confirmed to be approximately 0.8. After IPTG (isopropyl-β-thiogalactopyranoside) was added to 1 mM, culturing was further continued for 4 to 5 hours, so that HyHEL-10 scFv SAcore was accumulated in the form of insoluble granules in the cells of *Escherichia coli*.

The cells were recovered from 250 ml of the culture solution, suspended in 20 ml of 20 mM tris hydrochloride, 30 mM NaCl, 5 mM EDTA at pH 7.5, and broken by ultrasonic disintegration at 60 W in an ice bath for 3 minutes. The obtained disrupted cell solution was subjected to centrifugation at 5° C. at 4400 g for 10 minutes, and 20 ml of the obtained precipitate was again suspended in 20 mM tris hydrochloride, 30 mM NaCl, and 5 mM EDTA at pH 7.5. The suspension was subjected to centrifugation at 5° C. at 6500 g for 10 minutes to obtain a precipitate. The same operation was further repeated one more time. Finally, 1.11 g of a precipitate containing insoluble granules of HyHEL-10 scFv SAcore was obtained.

Experiment 12

(1) In the same manner as in Experiment 2, 1.11 g of the HyHEL-10 scFv SAcore precipitate obtained in Reference Example 3 was solubilized, and 4.75 ml of a solubilized solution was obtained. Nevertheless, finally, the concentration of lauroyl-L-Glu contained therein was adjusted to 2.5%.

(2) A diluting solution containing arginine hydrochloride was prepared.

(3) Of 4.75 ml of the solubilized solution obtained in (1), 2.9 ml was diluted 50 fold with the above diluting solution. Finally, 145 ml of 0.05% lauroyl-L-Glu, 1.2 M arginine hydrochloride, 1 mM EDTA, and 80 mM tris hydrochloride was prepared, with pH 7.6. The concentration of the protein was adjusted to 0.05 mg/ml. In the case of the HyHEL-10 scFv SAcore, intramolecular disulfide bond formation was already in progress. Hence, there was no need for a reaction facilitating the disulfide bond formation with a redox reagent such as glutathione.

(4) After being maintained at 5° C. for 18 hours, the solution obtained in (3) was concentrated to 50 ml using an ultrafiltration membrane (Pellicon 3, NMWL of 10 kDa; manufactured by Millipore Corporation).

(5) This was loaded separately twice, each 25 ml, onto a Sephadex G-25 column (5 cmφ×6.5 cm; manufactured by GE Healthcare) equilibrated in advance with a buffer (50 mM tris hydrochloride, 0.2 M arginine hydrochloride, 1 mM EDTA, pH 7.8), and subsequently deployed using the same buffer. Thereby, a protein fraction was obtained using UV absorption at 280 nm as an indicator. Thus, the concentrated solution in the column was replaced with the buffer.

(6) After the protein fraction was maintained at 5° C. for 3 days, a total of 68 ml thereof was concentrated approximately 3 fold in concentration to 15 ml using an ultrafiltration membrane (Amicon Ultra-15, regenerated cellulose membrane, NMWL of 10 kDa; manufactured by Millipore Corporation).

(7) This was diluted 6 fold with a buffer (20 mM tris hydrochloride, 0.2 M NaCl, pH 8.0), adjusted to 90 ml, and loaded onto an anion exchange column (HiTrap Q HP, 5 ml; manufactured by GE Healthcare) equilibrated in advance with the same buffer to thereby recover the total amount, 95 ml, of a fraction having flowed through the column from which the aggregate was removed. The resultant was maintained at 5° C. for 1 day. The total amount was concentrated to 10 ml using an ultrafiltration membrane (Amicon Ultra-15, regenerated cellulose membrane, NMWL of 30 kDa; manufactured by Millipore Corporation). Quantification by gel filtration HPLC confirmed 1.2 mg of a HyHEL-10 scFv SAcore multimeric protein. This was maintained at 5° C. for 2 days.

(8) Of 10 ml of the concentrated solution, 5 ml was diluted 10 fold with a buffer (20 mM tris hydrochloride, pH 8.0) and adjusted to 50 ml. This was loaded onto an anion exchange column (HiTrap Q HP, 5 ml; manufactured by GE Healthcare) equilibrated in advance with the same buffer, and subjected to linear concentration gradient elution at a flow rate of 2.5 ml/min to an elution buffer (20 mM tris hydrochloride, 0.5 M NaCl, pH 8.0) for 20 minutes. Using UV absorption at 280 nm as an indicator, 6.5 ml of a protein fraction was obtained.

The remaining concentrated solution, 5 ml, was similarly treated, and 7.8 ml of a protein fraction was obtained. The two protein fractions were put together, and concentrated to 2 ml using an ultrafiltration membrane (Amicon Ultra-15, regenerated cellulose membrane, NMWL of 30 kDa; manufactured by Millipore Corporation). Quantification by gel filtration HPLC confirmed 0.76 mg of the HyHEL-10 scFv SAcore multimeric protein. This was maintained at 5° C. for 2 days.

(9) Then, 2 ml of the concentrated solution was loaded onto Superdex 200 pg 16/60 (2.6 cmφ×60 cm; manufactured by GE Healthcare) equilibrated in advance with a buffer (50 mM tris hydrochloride, 0.2 M NaCl, 1 mM EDTA, pH 8.0) to recover the HyHEL-10 scFv SAcore multimeric protein using UV absorption at 280 nm as an indicator. The resultant was concentrated to 1 ml using an ultrafiltration membrane (Amicon Ultra-15, regenerated cellulose membrane, NMWL of 30 kDa; manufactured by Millipore Corporation). Quantification by gel filtration HPLC confirmed 0.39 mg of the HyHEL-10 scFv SAcore multimeric protein.

The total recovery rate from the solubilized solution was 5.3%.

Figure 5:
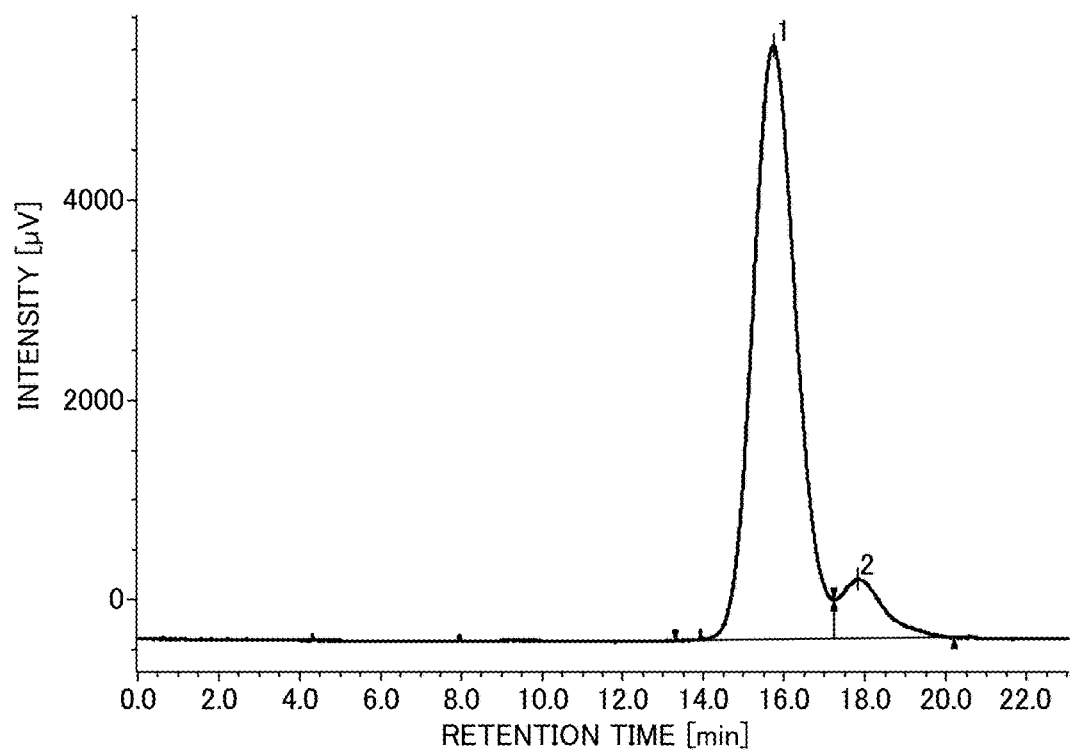
FIG. 5 is a graph showing a gel filtration HPLC pattern (column, Superdex 10/300 GL; eluent, 0.1 M sodium phosphate, 0.2 M arginine hydrochloride, pH 6.8; flow rate, 0.8 ml/min; detection, UV absorption at 280 nm) of a HyHEL-10 scFv SAcore multimeric protein purified in Experiment 12. A minor component seen behind the peak is assumed to be a decomposition product of the HyHEL-10 scFv SAcore multimeric protein.
Figure 6:
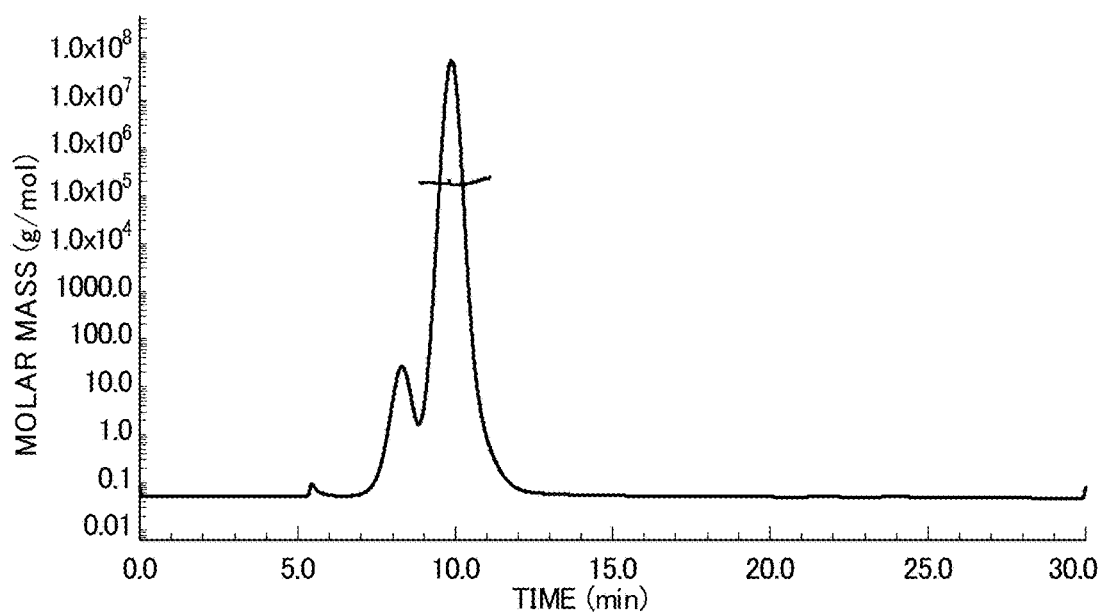
FIG. 6 is a graph showing a field flow fractionation pattern (cross flow, 2.7 ml/min; channel flow, 1.5 ml/min; eluent, 0.1 M sodium phosphate, pH 6.8; UV absorption at 225 nm) of the HyHEL-10 scFv SAcore multimeric protein purified in Experiment 12. The molecular weight was calculated using a multiangle light scattering detector and the Zimm plot method. A minor component seen in front of the peak is assumed to be a decomposition product of the HyHEL-10 scFv SAcore multimeric protein.
Figure 7:
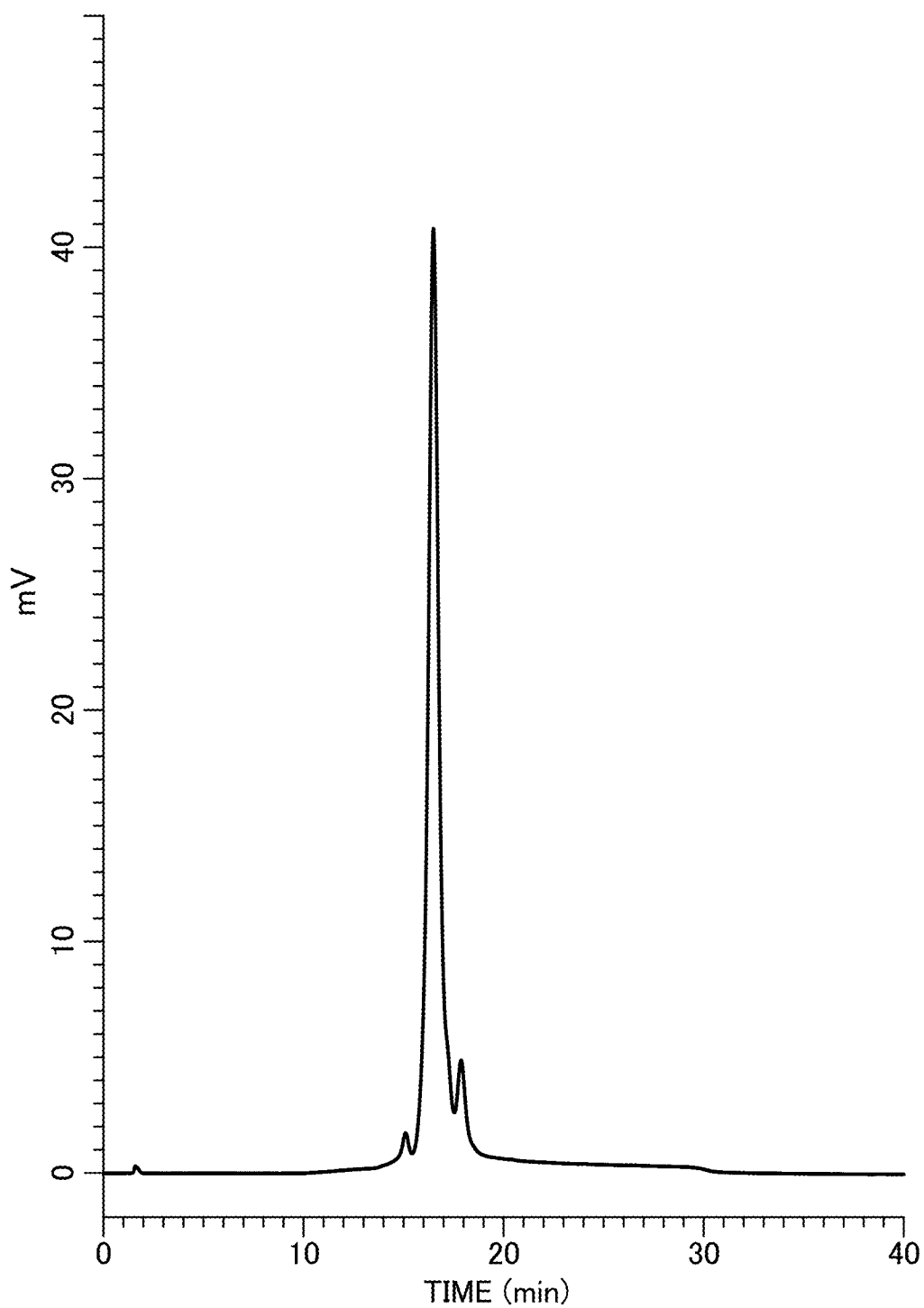
FIG. 7 is a graph showing an anion exchange HPLC pattern (column, resource Q, 1 ml; flow rate, 0.5 ml/min; eluent, 20 mM tris hydrochloride, pH 8.0, elution method, 0 to 0.5 M NaCl linear concentration gradient elution, 20 minutes; detection, UV absorption at 280 nm) of the HyHEL-10 scFv SAcore multimeric protein purified in Experiment 12. Minor components seen in front of and behind of the peak are assumed to be decomposition products of the HyHEL-10 scFv SAcore multimeric protein.

The purified HyHEL-10 scFv SAcore multimeric protein provides a sharp peak indicating a high monodispersity in gel filtration HPLC (FIG. 5), while providing a molecular weight of 178 kDa in a field flow fractionation/static light-scattering method using an eluent of 0.1 M sodium phosphate at pH 6.8 (FIG. 6). A single sharp peak was demonstrated in anion exchange HPLC using resource Q, 1 ml (manufactured by GE Healthcare) (FIG. 7).

From the above, it was concluded that the HyHEL-10 scFv SAcore multimeric protein having a tetrameric structure as expected was obtained.

(10) The inhibitory activity of the purified HyHEL-10 scFv SAcore multimeric protein on an egg white lysozyme enzyme was examined according to the published report (Ueda et al, Gene. 1993, 129, 129-34.).

Using a buffer for measurement (50 mM phosphate buffer, 12 mM NaCl, pH 6.2), mixture solutions, each 100 µl, were prepared in which the final concentration of a hen egg white lysozyme (Code No. L-6876, manufactured by Sigma-Aldrich Corporation) was adjusted to 0.09 µM, whereas the final concentration of the purified HyHEL-10 scFv SAcore multimeric protein was adjusted to seven levels from 0.0056 to 0.045 µM. The mixture solutions were maintained at 28° C. for 30 minutes. Since the purified HyHEL-10 scFv SAcore multimeric protein has four anti-lysozyme antibody domains (HyHEL-10 scFvs) in a molecule thereof, the molar mixing ratio of lysozyme:HyHEL-10 scFv in these mixture solutions corresponds to 1:0.25 to 1:2.

As a positive control of the lysozyme activity, a mixture solution was prepared in which no purified HyHEL-10 scFv SAcore multimeric protein was added.

To 100 µl of each of the mixture solutions, 100 µl of a microbial suspension (*Micrococcus lisodeikicus*, ATCC4698, SIGMA M-3770, manufactured by Sigma-Aldrich Corporation) was added. The microbial suspension had been adjusted with 50 mM phosphate buffer at pH 6.2, so that the suspension had an absorbance of 1.78 at 540 nm. Immediately thereafter, the absorbance was measured at a measurement wavelength of 540 nm at 28° C. every minutes for 1 hour. The relation between the molar mixing ratio of the purified HyHEL-10 scFv SAcore multimeric protein to hen lysozyme and the lysozyme activity inhibition ratio was examined, with the percentage of the absorbance decreased (slope) at each measurement point being regarded as the lysozyme activity.

Figure 8:
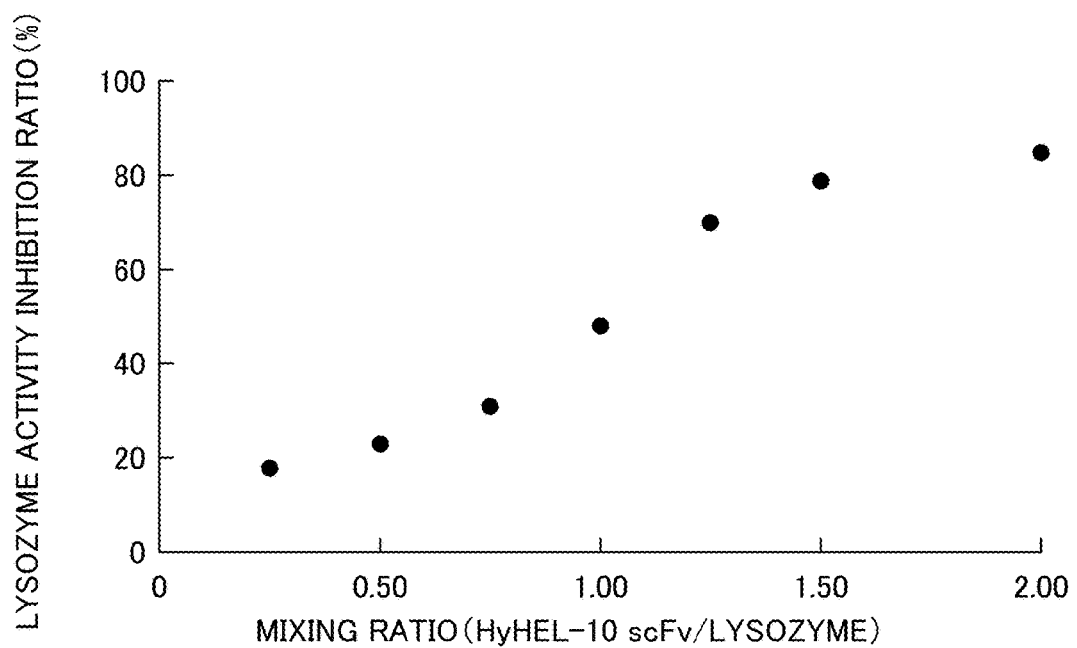
FIG. 8 is a graph showing a hen egg white lysozyme activity inhibition ratio of the HyHEL-10 scFv SAcore multimeric protein purified in Experiment 12. The lysozyme and the HyHEL-10 scFv SAcore multimeric protein were mixed at a ratio shown in the graph, and added to a microbial suspension serving as the substrate of the lysozyme. Based on a percentage change in the absorbance, a remaining lysozyme activity was evaluated. An inhibition ratio (%) was determined relative to a lysozyme activity exhibited when no HyHEL-10 scFv SAcore multimeric protein was added.

When the molar mixing ratio of hen lysozyme:HyHEL-10 scFv was 1:1, 50% of the lysozyme activity was inhibited. When the molar mixing ratio was 1:2, the lysozyme activity was almost inhibited (FIG. 8).

This suggests that among four scFvs in one molecule of the HyHEL-10 scFv SAcore multimeric protein, two scFvs have an ability to bind to the lysozyme and inhibit the activity.

The binding ability of the purified HyHEL-10 scFv SAcore multimeric protein to an egg white lysozyme was examined by a field flow fractionation/static light-scattering method using an eluent of 0.1 M sodium phosphate at pH 6.8.

Using a buffer (50 mM TrisHCl, 0.2 M NaCl, 1 mM EDTA, pH 8.0), mixture solutions, each 600 µl, were prepared in which the final concentration of the purified HyHEL-10 scFv SAcore multimeric protein was adjusted to 1.24 µM, whereas the final concentration of the hen egg white lysozyme was adjusted to three levels of none, 2.48 µM, and 4.95 µM. Since the purified HyHEL-10 scFv SAcore multimeric protein has four anti-lysozyme antibody domains (HyHEL-10 scFvs) in a molecule thereof, the molar mixing ratios of lysozyme:HyHEL-10 scFv in these mixture solutions respectively correspond to 0:1, 0.5:1, and 1:1. After each of the mixture solutions was maintained at 5° C. for 24 hours, 70 µl thereof was subjected to the field flow fractionation, and changes in the peak retention time and in the molecular weight by the static light-scattering method were traced.

As the lysozyme mixing ratio was increased, the peak retention time was extended, which supported the increase in the molecular size due to binding to the lysozyme. The molecular weight was calculated to be 163.4 kDa, 188.1 kDa, and 225.0 kDa, respectively indicating that 0 molecules (no lysozyme), 1.7 molecules, and 4.3 molecules of the hen egg white lysozyme bound to one molecule of the purified HyHEL-10 scFv SAcore multimeric protein.

This revealed that one molecule of the purified HyHEL-10 scFv SAcore multimeric protein having a tetravalent binding ability is capable of binding to four molecules of a lysozyme as designed. Nonetheless, it was revealed that, as described in the enzymatic activity inhibition evaluation in (10) above, molecules whose lysozyme activity was actually inhibited are only two, which correspond to half of the bound lysozyme molecules.

Experiment 13

(1) Using a diluting solution containing arginine hydrochloride, 0.15 ml of the same HyHEL-10 scFv SAcore solubilized solution as in Experiment 12 was diluted 50 fold. Finally, prepared was 7.5 ml of 0.05% lauroyl-L-Glu, 1.2 M arginine hydrochloride, 1 mM EDTA, and 80 mM tris hydrochloride, with pH 7.6. The concentration of the protein was adjusted to 0.03 mg/ml.

After being maintained at 5° C. for 18 hours, the obtained solution was concentrated to 2.5 ml using an ultrafiltration membrane (Amicon Ultra-15, regenerated cellulose membrane, NMWL of 10 kDa; manufactured by Millipore Corporation), loaded onto a PD-10 column (manufactured by GE Healthcare) equilibrated in advance with a buffer (50 mM tris hydrochloride, 0.3 M arginine hydrochloride, 1 mM EDTA, pH 7.8), and deployed using 3 ml of the same buffer. Thereby, the total amount was recovered. Thus, the concentrated solution in the column was replaced with the buffer.

After being maintained at 5° C. for 1 day, the obtained protein fraction was concentrated 3 fold in concentration to 1 ml using an ultrafiltration membrane (Amicon Ultra-4, regenerated cellulose membrane, NMWL of 10 kDa; manufactured by Millipore Corporation), and maintained at 5° C. for 2 days. This was diluted 6 fold with a buffer (20 mM tris hydrochloride, 0.2 M NaCl, pH 8.0) and adjusted to 6 ml. The resultant was loaded onto an anion exchange column (HiTrap Q HP, 1 ml; manufactured by GE Healthcare) equilibrated in advance with the same buffer to thereby recover the total amount, 7 ml, of a fraction having flowed through the column from which the aggregate was removed.

Immediately thereafter, the resultant was concentrated 7 fold in concentration to 1 ml using an ultrafiltration membrane (Amicon Ultra-4, regenerated cellulose membrane, NMWL of 10 kDa; manufactured by Millipore Corporation). Quantification by gel filtration HPLC confirmed 0.038 mg of a HyHEL-10 scFv SAcore multimeric protein. The total recovery rate from the solubilized solution was 17.0%.

(2) Non-reducing SDS-PAGE was carried out on samples in the solubilization stage, the 50-fold dilution stage with the diluting buffer containing arginine hydrochloride, the replacement stage with the buffer containing arginine hydrochloride using the PD-10 column, and the purification stage using the anion exchange column so as to confirm an operation stage when the tetrameric structure was formed.

In this SDS-PAGE, moderate heating conditions of 45° C. and 2 minutes were set for pretreating the samples in order to observe a tetramer band of a tetrameric structure, which was already formed without being dissociated after the samples were diluted and adjusted to 0.03 µg/ml using a diluting buffer containing 2% SDS. In the SDS-PAGE analysis in which samples are treated under such moderate heating conditions, the tetrameric structure of natural core Streptavidin can be observed without being disrupted, as described in a published report (Jody Schultz, Donald. Axworthy et al, Cancer Research 60, 6663-6669 (2000)) and so forth.

Figure 9:
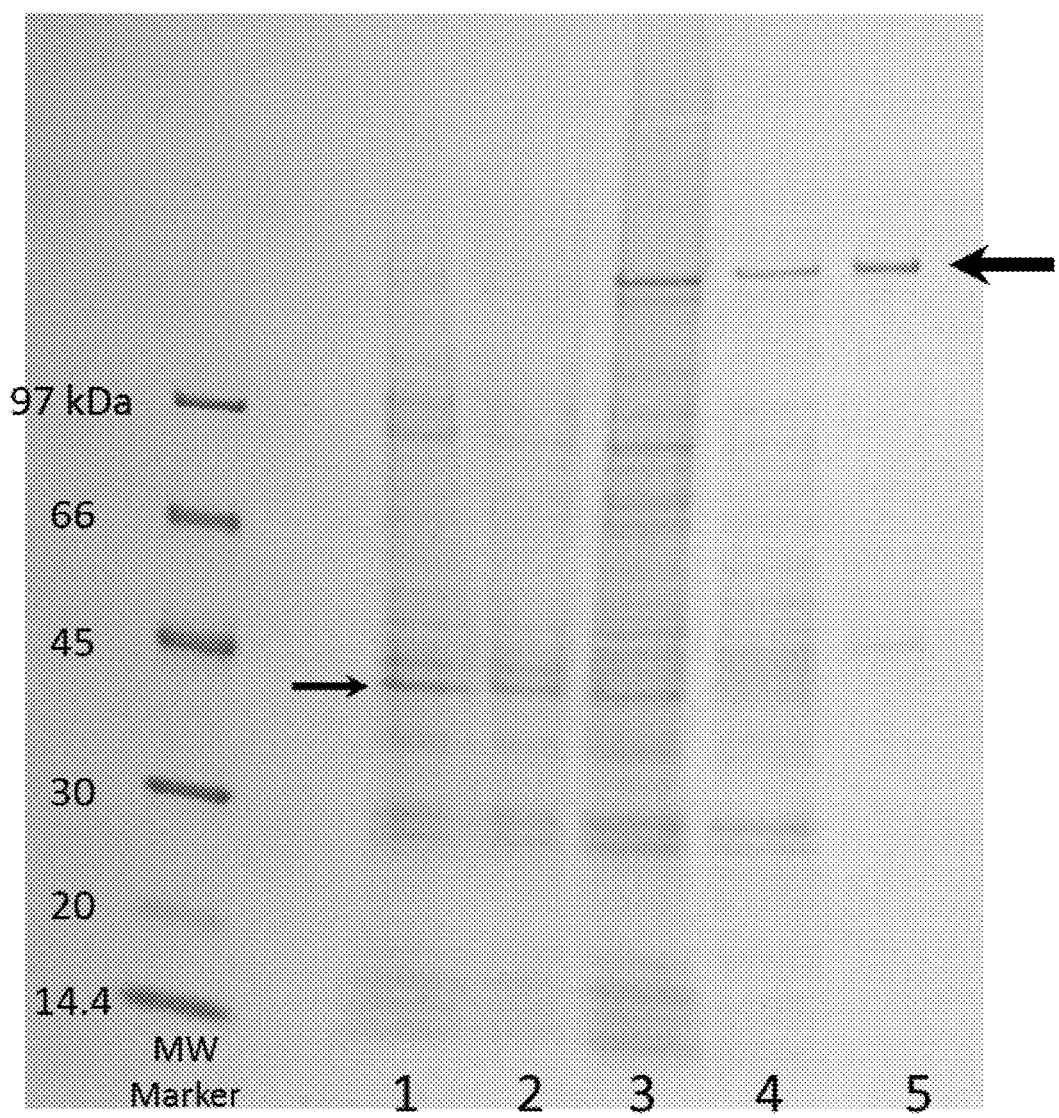
FIG. 9 is to analyze a refolding step carried out on the HyHEL-10 scFv SAcore multimeric protein in Experiment 13 by SDS-PAGE (non-reducing). Lane 1, an extraction step; lane 2, a 50-fold dilution stage with a diluting buffer; lane 3, a replacement stage with a buffer containing arginine hydrochloride; lane 4, a purification stage using an anion exchange column; lane 5, a purified HyHEL-10 scFv SAcore multimeric protein obtained in Experiment 12. The broad arrow (←) indicates a band of the tetramer, while the thin arrow (→) indicates a band of a monomer.

As shown in FIG. 9, in the solubilization stage and the 50-fold dilution stage with the diluting buffer containing arginine hydrochloride, no band of the HyHEL-10 scFv SAcore multimeric protein was observed. It was found that the first time the tetrameric structure was formed was in the replacement stage with the buffer containing arginine hydrochloride when lauroyl-L-Glu was completely removed (the band indicated by ← in the figure).

This specifically shows the characteristics of the present invention that: at first, only formation of a subunit structure is allowed to progress by inhibiting the association of subunits using lauroyl-L-Glu, and thereafter lauroyl-L-Glu is replaced with a buffer and removed, consequently facilitating the association of the subunits and achieving completion of folding.

The invention claimed is:

1. A method for producing a multimeric protein consisting of two or more monomeric protein, wherein said monomeric protein is obtained by fusing a protein having an immunoglobulin fold structure to either a protein or a functional fragment thereof that can serve as a subunit structure, the method comprising the steps of:
 (A) preparing a monomeric protein having an insoluble granular form in cells of a microorganism, the monomeric protein obtained by fusing a first protein having an immunoglobulin fold structure to a second different protein that can serve as a subunit structure;
 (B) solubilizing the monomeric protein prepared in step (A) with an aqueous solution comprising lauroyl glutamic acid and/or a salt thereof, resulting in a first solution;
 (C) adding a phosphate buffer to the first solution obtained in step (B) so that the concentration of the lauroyl glutamic acid and/or salt thereof is 2 to 5%;
 (D) diluting the solution obtained in step (C) in a buffer comprising arginine and/or an arginine derivative to lower the concentration of lauroyl glutamic acid and/or a salt thereof, resulting in a second solution; and
 (E) replacing a solvent of the second solution obtained in step (C) with a buffer, resulting in removal said lauroyl glutamic acid and/or a salt thereof, using a method selected from the group consisting of:
  (e1) column chromatography selected from the group consisting of gel filtration chromatography, ion-exchange chromatography, hydrophobic interaction chromatography, and combination thereof;
  (e2) ultrafiltration;
  (e3) dialysis; and
  (e4) combinations thereof.

2. The method according to claim 1, wherein the monomeric protein is a fusion protein of scFv and streptavidin.

3. The method according to claim 2, wherein the scFv is selected from the group consisting of HyHEL-10 scFv and D1.3 scFv.

4. The method according to claim 2, wherein the streptavidin is full length streptavidin or a functional fragment thereof.

5. The method according to claim 1, wherein the arginine derivative is selected from the group consisting of arginine having an acyl group with 1 to 6 carbon atoms, arginine butyl ester, agmatine, and argininic acid.

6. The method according to claim 1, wherein the arginine is arginine hydrochloride.

* * * * *